(12) United States Patent
Barron et al.

(10) Patent No.: US 8,206,376 B2
(45) Date of Patent: Jun. 26, 2012

(54) CONNECTION SYSTEM FOR MULTI-LUMEN CATHETER

(75) Inventors: William R. Barron, Riverton, UT (US); Jeffrey D. Bright, Stansbury Park, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/974,818

(22) Filed: Dec. 21, 2010

(65) Prior Publication Data

US 2011/0098679 A1    Apr. 28, 2011

Related U.S. Application Data

(62) Division of application No. 11/471,193, filed on Jun. 20, 2006, now Pat. No. 7,875,019.

(60) Provisional application No. 60/692,180, filed on Jun. 20, 2005.

(51) Int. Cl.
    *A61M 25/16* (2006.01)
(52) U.S. Cl. ..................................................... 604/533
(58) Field of Classification Search .......... 604/533–535, 604/43–45, 288.01–288.04, 538–539
    See application file for complete search history.

(56) References Cited

U.S. PATENT DOCUMENTS

| | | | |
|---|---|---|---|
| 2,471,623 A | 5/1949 | Hubbell | |
| 2,709,542 A | 5/1955 | Eller | |
| 3,176,690 A | 4/1965 | H'Doubler | |
| D217,795 S | 6/1970 | Spaven | |
| 3,527,226 A | 9/1970 | Hakim | |
| 3,565,078 A | 2/1971 | Vailliancourt et al. | |
| 3,572,340 A | 3/1971 | Lloyd et al. | |
| 3,650,507 A | 3/1972 | Nyberg et al. | |
| 3,672,372 A | 6/1972 | Heimlich | |
| 3,805,794 A | 4/1974 | Schlesinger | |
| 3,921,631 A | 11/1975 | Thompson | |
| 4,000,739 A | 1/1977 | Stevens | |
| 4,029,095 A | 6/1977 | Pena et al. | |
| 4,068,659 A | 1/1978 | Moorehead | |
| 4,112,949 A | 9/1978 | Rosenthal et al. | |
| 4,123,091 A | 10/1978 | Cosentino et al. | |
| 4,134,402 A | 1/1979 | Mahurkar | |
| 4,198,973 A | 4/1980 | Millet | |

(Continued)

FOREIGN PATENT DOCUMENTS

EP    0183396 A1    6/1986

(Continued)

OTHER PUBLICATIONS

Arrow® Cannon™ II Plus Product Brochure, Feb. 2012.

(Continued)

*Primary Examiner* — Theodore Stigell
(74) *Attorney, Agent, or Firm* — Rutan & Tucker, LLP

(57) ABSTRACT

A catheter connection system and a method of connecting the catheter connection system to a catheter. The catheter connection system includes a hub assembly and a collar. The hub assembly includes a cannula extending from a distal end thereof, and a collet defining an inner surface spaced apart from the cannula to permit passage of a catheter wall between the body and the cannula. The collet includes a proximal barb on an outer surface and the collar includes an attachment barb on an inner surface, engagement of the respective barbs acting to provide a permanent connection between the collar on the collet, while permitting free rotation of the collar about the collet.

19 Claims, 17 Drawing Sheets

U.S. PATENT DOCUMENTS

| | | |
|---|---|---|
| 4,233,974 A | 11/1980 | Desecki et al. |
| 4,235,232 A | 11/1980 | Spaven et al. |
| 4,256,106 A | 3/1981 | Shoor |
| 4,256,116 A | 3/1981 | Meretsky et al. |
| 4,267,835 A | 5/1981 | Barger et al. |
| 4,296,747 A | 10/1981 | Ogle |
| 4,306,562 A | 12/1981 | Osborne |
| 4,340,052 A | 7/1982 | Dennehey et al. |
| 4,387,879 A | 6/1983 | Tauschinski et al. |
| 4,391,029 A | 7/1983 | Czuba et al. |
| 4,411,654 A | 10/1983 | Boarini et al. |
| 4,412,832 A | 11/1983 | Kling et al. |
| 4,424,833 A | 1/1984 | Spector et al. |
| D272,651 S | 2/1984 | Mahurkar |
| 4,430,081 A | 2/1984 | Timmermans |
| 4,431,426 A | 2/1984 | Groshong et al. |
| 4,432,759 A | 2/1984 | Gross et al. |
| 4,436,519 A | 3/1984 | O'Neill |
| 4,439,179 A | 3/1984 | Lueders et al. |
| 4,445,893 A | 5/1984 | Bodicky |
| 4,449,973 A | 5/1984 | Luther |
| 4,468,224 A | 8/1984 | Enzmann et al. |
| 4,473,067 A | 9/1984 | Schiff |
| 4,490,003 A | 12/1984 | Robinson |
| RE31,855 E | 3/1985 | Osborne |
| 4,502,502 A | 3/1985 | Krug |
| 4,512,766 A | 4/1985 | Vailancourt |
| 4,535,818 A | 8/1985 | Duncan et al. |
| 4,539,003 A | 9/1985 | Tucker |
| 4,543,087 A | 9/1985 | Sommercorn et al. |
| 4,553,959 A | 11/1985 | Hickey et al. |
| 4,557,261 A | 12/1985 | Rugheimer et al. |
| 4,568,329 A | 2/1986 | Mahurkar |
| 4,571,241 A | 2/1986 | Christopher |
| 4,573,974 A | 3/1986 | Ruschke |
| 4,581,012 A | 4/1986 | Brown et al. |
| 4,581,025 A | 4/1986 | Timmermans |
| 4,583,968 A | 4/1986 | Mahurkar |
| 4,591,355 A | 5/1986 | Hilse |
| 4,592,749 A | 6/1986 | Ebling et al. |
| 4,596,559 A | 6/1986 | Fleischhacker |
| 4,596,571 A | 6/1986 | Bellotti et al. |
| 4,610,665 A | 9/1986 | Matsumoto et al. |
| 4,619,643 A | 10/1986 | Bai |
| 4,623,327 A | 11/1986 | Mahurkar |
| 4,626,245 A | 12/1986 | Weinstein |
| 4,643,711 A | 2/1987 | Bates |
| 4,650,472 A | 3/1987 | Bates |
| 4,673,393 A | 6/1987 | Suzuki et al. |
| 4,675,004 A | 6/1987 | Hadford et al. |
| 4,675,020 A | 6/1987 | McPhee |
| 4,681,122 A | 7/1987 | Winters et al. |
| 4,682,978 A | 7/1987 | Martin et al. |
| 4,692,141 A | 9/1987 | Mahurkar |
| 4,701,159 A | 10/1987 | Brown et al. |
| 4,722,725 A | 2/1988 | Sawyer et al. |
| 4,723,550 A | 2/1988 | Bales et al. |
| 4,723,948 A | 2/1988 | Clark et al. |
| 4,726,374 A | 2/1988 | Bales et al. |
| 4,738,658 A | 4/1988 | Magro et al. |
| 4,743,265 A | 5/1988 | Whitehouse et al. |
| 4,747,833 A | 5/1988 | Kousai et al. |
| 4,753,765 A | 6/1988 | Pande |
| 4,770,652 A | 9/1988 | Mahurkar |
| 4,772,266 A | 9/1988 | Groshong |
| 4,772,268 A | 9/1988 | Bates |
| 4,776,841 A | 10/1988 | Catalano |
| 4,784,644 A | 11/1988 | Sawyer et al. |
| 4,795,426 A | 1/1989 | Jones |
| 4,798,594 A | 1/1989 | Hillstead |
| 4,808,155 A | 2/1989 | Mahurkar |
| 4,842,582 A | 6/1989 | Mahurkar |
| 4,842,592 A | 6/1989 | Caggiani et al. |
| 4,850,955 A | 7/1989 | Newkirk |
| 4,865,593 A | 9/1989 | Ogawa et al. |
| 4,874,377 A | 10/1989 | Newgard et al. |
| 4,895,561 A | 1/1990 | Mahurkar |
| 4,895,570 A | 1/1990 | Larkin |
| 4,898,669 A | 2/1990 | Tesio |
| 4,909,798 A | 3/1990 | Fleischhacker et al. |
| RE33,219 E | 5/1990 | Daniell et al. |
| 4,921,479 A | 5/1990 | Grayzel |
| 4,929,235 A | 5/1990 | Merry et al. |
| 4,929,236 A | 5/1990 | Sampson |
| 4,932,633 A | 6/1990 | Johnson et al. |
| 4,932,938 A | 6/1990 | Goldberg et al. |
| 4,935,010 A | 6/1990 | Cox et al. |
| 4,936,826 A | 6/1990 | Amarasinghe |
| 4,946,133 A | 8/1990 | Johnson et al. |
| 4,946,449 A | 8/1990 | Davis, Jr. |
| 4,952,359 A | 8/1990 | Wells |
| 4,960,412 A | 10/1990 | Fink |
| 4,966,588 A | 10/1990 | Rayman et al. |
| 4,983,168 A | 1/1991 | Moorehead |
| 4,997,424 A | 3/1991 | Little |
| 5,007,901 A | 4/1991 | Shields |
| 5,035,686 A | 7/1991 | Crittenden et al. |
| 5,041,095 A | 8/1991 | Littrell |
| 5,053,003 A | 10/1991 | Dadson et al. |
| 5,053,004 A | 10/1991 | Markel et al. |
| 5,053,013 A | 10/1991 | Ensminger et al. |
| 5,053,014 A | 10/1991 | Van Heugten |
| 5,053,023 A | 10/1991 | Martin |
| 5,057,073 A | 10/1991 | Martin |
| 5,059,170 A | 10/1991 | Cameron |
| 5,064,414 A | 11/1991 | Revane |
| 5,066,285 A | 11/1991 | Hillstead |
| 5,071,411 A | 12/1991 | Hillstead |
| 5,078,688 A | 1/1992 | Lobodzinski et al. |
| 5,085,645 A | 2/1992 | Purdy et al. |
| 5,092,857 A | 3/1992 | Fleischhacker |
| 5,098,392 A | 3/1992 | Fleischhacker et al. |
| 5,098,393 A | 3/1992 | Amplatz et al. |
| 5,106,368 A | 4/1992 | Uldall et al. |
| 5,108,380 A | 4/1992 | Herlitze et al. |
| 5,112,301 A | 5/1992 | Fenton, Jr. et al. |
| 5,112,323 A | 5/1992 | Winkler et al. |
| 5,114,408 A | 5/1992 | Fleischhaker et al. |
| 5,117,836 A | 6/1992 | Millar |
| 5,125,904 A | 6/1992 | Lee |
| 5,135,599 A | 8/1992 | Martin et al. |
| 5,137,524 A | 8/1992 | Lynn et al. |
| 5,141,497 A | 8/1992 | Erskine |
| 5,149,327 A | 9/1992 | Oshiyama et al. |
| 5,154,701 A | 10/1992 | Cheer et al. |
| 5,156,592 A | 10/1992 | Martin et al. |
| 5,156,596 A | 10/1992 | Balbierz et al. |
| 5,158,545 A | 10/1992 | Trudell et al. |
| 5,158,553 A | 10/1992 | Berry et al. |
| 5,160,323 A | 11/1992 | Andrew et al. |
| 5,163,903 A | 11/1992 | Crittenden et al. |
| 5,167,634 A | 12/1992 | Corrigan, Jr. et al. |
| 5,167,637 E | 12/1992 | Okada et al. |
| 5,169,393 A | 12/1992 | Moorehead et al. |
| 5,171,222 A | 12/1992 | Euteneuer et al. |
| 5,180,372 A | 1/1993 | Vegoe et al. |
| 5,186,431 A | 2/1993 | Tamari |
| 5,188,593 A | 2/1993 | Martin |
| 5,190,520 A | 3/1993 | Fenton, Jr. et al. |
| 5,190,528 A | 3/1993 | Fonger et al. |
| 5,190,529 A | 3/1993 | McCrory et al. |
| 5,191,898 A | 3/1993 | Millar |
| 5,195,962 A | 3/1993 | Martin et al. |
| 5,197,951 A | 3/1993 | Mahurkar |
| 5,197,976 A | 3/1993 | Herweck et al. |
| 5,201,722 A | 4/1993 | Moorehead et al. |
| 5,205,834 A | 4/1993 | Moorehead et al. |
| 5,207,650 A | 5/1993 | Martin |
| 5,209,723 A | 5/1993 | Twardowski et al. |
| 5,211,633 A | 5/1993 | Stouder, Jr. |
| 5,215,538 A | 6/1993 | Larkin |
| 5,221,255 A | 6/1993 | Mahurkar et al. |
| 5,221,256 A | 6/1993 | Mahurkar |
| 5,221,263 A | 6/1993 | Sinko et al. |
| 5,234,410 A | 8/1993 | Graham et al. |
| 5,242,413 A | 9/1993 | Heiliger |
| 5,242,430 A | 9/1993 | Arenas et al. |

| Patent | Date | Inventor |
|---|---|---|
| 5,250,033 A | 10/1993 | Evans et al. |
| 5,251,873 A | 10/1993 | Atkinson et al. |
| 5,255,691 A | 10/1993 | Otten |
| 5,273,540 A | 12/1993 | Luther et al. |
| 5,273,546 A | 12/1993 | McLaughlin et al. |
| 5,275,583 A | 1/1994 | Crainich |
| 5,279,597 A | 1/1994 | Dassa et al. |
| 5,290,294 A | 3/1994 | Cox et al. |
| 5,304,142 A | 4/1994 | Liebl et al. |
| 5,304,156 A | 4/1994 | Sylvanowicz et al. |
| 5,312,337 A | 5/1994 | Flaherty et al. |
| 5,312,355 A | 5/1994 | Lee |
| 5,312,357 A | 5/1994 | Buijs et al. |
| 5,320,602 A | 6/1994 | Karpiel |
| 5,324,271 A | 6/1994 | Abiuso et al. |
| 5,324,274 A | 6/1994 | Martin |
| 5,330,437 A | 7/1994 | Durman |
| 5,334,157 A | 8/1994 | Klein et al. |
| 5,334,187 A | 8/1994 | Fischell et al. |
| 5,336,192 A | 8/1994 | Palestrant |
| 5,338,313 A | 8/1994 | Mollenauer et al. |
| 5,342,386 A | 8/1994 | Trotta |
| 5,348,537 A | 9/1994 | Wiesner et al. |
| 5,350,358 A | 9/1994 | Martin |
| 5,350,362 A | 9/1994 | Stouder, Jr. |
| 5,350,363 A | 9/1994 | Goode et al. |
| 5,360,397 A | 11/1994 | Pinchuk |
| 5,360,403 A | 11/1994 | Mische |
| 5,364,393 A | 11/1994 | Auth et al. |
| 5,368,574 A | 11/1994 | Antonacci et al. |
| 5,374,245 A | 12/1994 | Mahurkar |
| 5,378,230 A | 1/1995 | Mahurkar |
| 5,380,276 A | 1/1995 | Miller et al. |
| 5,382,241 A | 1/1995 | Choudhury et al. |
| 5,389,090 A | 2/1995 | Fischell et al. |
| 5,391,152 A | 2/1995 | Patterson |
| 5,395,352 A | 3/1995 | Penny |
| 5,397,311 A | 3/1995 | Walker et al. |
| 5,399,172 A | 3/1995 | Martin et al. |
| 5,401,245 A | 3/1995 | Haining |
| 5,405,320 A | 4/1995 | Twardowski et al. |
| 5,405,323 A | 4/1995 | Rogers et al. |
| 5,405,341 A | 4/1995 | Martin |
| 5,407,434 A | 4/1995 | Gross |
| 5,409,463 A | 4/1995 | Thomas et al. |
| 5,409,464 A | 4/1995 | Villalobos |
| 5,409,469 A | 4/1995 | Schaerf |
| 5,409,644 A | 4/1995 | Martin et al. |
| 5,413,561 A | 5/1995 | Fischell et al. |
| 5,415,320 A | 5/1995 | North et al. |
| 5,417,668 A | 5/1995 | Setzer et al. |
| 5,419,340 A | 5/1995 | Stevens |
| 5,423,762 A | 6/1995 | Hillstead |
| 5,429,616 A | 7/1995 | Schaffer |
| 5,437,645 A | 8/1995 | Urban et al. |
| 5,441,504 A | 8/1995 | Pohndorf et al. |
| 5,445,613 A | 8/1995 | Orth |
| 5,453,095 A | 9/1995 | Davila et al. |
| 5,454,409 A | 10/1995 | McAffer et al. |
| 5,460,616 A | 10/1995 | Weinstein et al. |
| 5,472,417 A | 12/1995 | Martin et al. |
| 5,472,418 A | 12/1995 | Palestrant |
| 5,472,432 A | 12/1995 | Martin |
| 5,472,435 A | 12/1995 | Sutton |
| 5,474,099 A | 12/1995 | Boehmer et al. |
| 5,474,540 A | 12/1995 | Miller et al. |
| 5,480,380 A | 1/1996 | Martin |
| 5,484,401 A | 1/1996 | Rodriguez et al. |
| 5,486,159 A | 1/1996 | Mahurkar |
| 5,488,960 A | 2/1996 | Toner |
| 5,496,299 A | 3/1996 | Felix et al. |
| 5,496,346 A | 3/1996 | Horzewski et al. |
| 5,501,676 A | 3/1996 | Niedospial et al. |
| 5,507,733 A | 4/1996 | Larkin et al. |
| 5,509,897 A | 4/1996 | Twardowski et al. |
| 5,509,902 A | 4/1996 | Raulerson |
| 5,514,117 A | 5/1996 | Lynn |
| 5,520,655 A | 5/1996 | Davila et al. |
| 5,520,665 A | 5/1996 | Fleetwood |
| 5,522,806 A | 6/1996 | Schonbachler et al. |
| 5,536,255 A | 7/1996 | Moss |
| 5,538,505 A | 7/1996 | Weinstein et al. |
| 5,542,931 A | 8/1996 | Gravener et al. |
| 5,556,387 A | 9/1996 | Mollenauer et al. |
| 5,569,182 A | 10/1996 | Twardowski et al. |
| 5,599,305 A | 2/1997 | Hermann et al. |
| 5,599,311 A | 2/1997 | Raulerson |
| 5,613,953 A | 3/1997 | Pohndorf |
| 5,613,956 A | 3/1997 | Patterson et al. |
| 5,624,413 A | 4/1997 | Markel et al. |
| 5,632,729 A | 5/1997 | Cai et al. |
| 5,636,875 A | 6/1997 | Wasser et al. |
| 5,637,102 A | 6/1997 | Tolkoff et al. |
| 5,647,857 A | 7/1997 | Anderson et al. |
| 5,651,776 A | 7/1997 | Appling et al. |
| 5,653,698 A | 8/1997 | Niedospial et al. |
| 5,672,158 A | 9/1997 | Okada et al. |
| 5,685,856 A | 11/1997 | Lehrer |
| 5,685,867 A | 11/1997 | Twardowski et al. |
| 5,702,370 A | 12/1997 | Sylvanowicz et al. |
| 5,702,374 A | 12/1997 | Johnson |
| 5,704,915 A | 1/1998 | Melsky et al. |
| 5,713,867 A | 2/1998 | Morris |
| 5,718,678 A | 2/1998 | Fleming, III |
| 5,718,692 A | 2/1998 | Schon et al. |
| 5,725,506 A | 3/1998 | Freeman et al. |
| 5,735,819 A | 4/1998 | Elliott |
| 5,741,233 A | 4/1998 | Riddle et al. |
| 5,752,937 A | 5/1998 | Otten et al. |
| 5,755,693 A | 5/1998 | Walker et al. |
| 5,755,702 A | 5/1998 | Hillstead et al. |
| 5,766,203 A | 6/1998 | Imran et al. |
| 5,772,628 A | 6/1998 | Bacich et al. |
| 5,772,643 A | 6/1998 | Howell et al. |
| 5,772,678 A | 6/1998 | Thomason et al. |
| 5,776,111 A | 7/1998 | Tesio |
| 5,782,505 A | 7/1998 | Brooks et al. |
| 5,782,807 A | 7/1998 | Falvai et al. |
| 5,782,817 A | 7/1998 | Franzel et al. |
| 5,785,694 A | 7/1998 | Cohen et al. |
| 5,797,869 A | 8/1998 | Martin et al. |
| 5,800,414 A | 9/1998 | Cazal |
| 5,807,311 A | 9/1998 | Palestrant |
| 5,810,789 A | 9/1998 | Powers et al. |
| 5,830,184 A | 11/1998 | Basta |
| 5,843,031 A | 12/1998 | Hermann et al. |
| 5,843,046 A | 12/1998 | Motisi et al. |
| 5,853,393 A | 12/1998 | Bogert |
| 5,858,007 A | 1/1999 | Fagan et al. |
| 5,865,721 A | 2/1999 | Andrews et al. |
| 5,879,333 A | 3/1999 | Smith et al. |
| 5,885,217 A | 3/1999 | Gisselberg et al. |
| 5,895,376 A | 4/1999 | Schwartz et al. |
| 5,897,533 A | 4/1999 | Glickman |
| 5,911,710 A | 6/1999 | Barry et al. |
| 5,916,194 A | 6/1999 | Jacobsen et al. |
| 5,919,160 A | 7/1999 | Sanfilippo, II |
| 5,921,968 A | 7/1999 | Lampropoulos et al. |
| 5,935,112 A | 8/1999 | Stevens et al. |
| 5,944,695 A | 8/1999 | Johnson et al. |
| 5,944,732 A | 8/1999 | Raulerson et al. |
| 5,947,953 A | 9/1999 | Ash et al. |
| 5,951,518 A | 9/1999 | Licata et al. |
| 5,957,912 A | 9/1999 | Heitzmann |
| 5,961,485 A | 10/1999 | Martin |
| 5,961,486 A | 10/1999 | Twardowski et al. |
| 5,967,490 A | 10/1999 | Pike |
| 5,971,958 A | 10/1999 | Zhang |
| 5,976,103 A | 11/1999 | Martin |
| 5,989,213 A | 11/1999 | Maginot |
| 5,997,486 A | 12/1999 | Burek et al. |
| 6,001,079 A | 12/1999 | Pourchez |
| 6,024,729 A | 2/2000 | Dehdashtian et al. |
| 6,027,480 A | 2/2000 | Davis et al. |
| 6,033,375 A | 3/2000 | Brumbach |
| 6,033,388 A | 3/2000 | Nordstrom et al. |
| 6,036,171 A | 3/2000 | Weinheimer et al. |
| 6,053,904 A | 4/2000 | Scribner et al. |

| Patent | Kind | Date | Inventor |
|---|---|---|---|
| 6,068,011 | A | 5/2000 | Paradis |
| 6,074,374 | A | 6/2000 | Fulton |
| 6,074,377 | A | 6/2000 | Sanfilippo, II |
| 6,074,379 | A | 6/2000 | Prichard |
| 6,083,207 | A | 7/2000 | Heck |
| 6,086,555 | A | 7/2000 | Eliasen et al. |
| 6,086,570 | A | 7/2000 | Aboul-Hosn et al. |
| 6,088,889 | A | 7/2000 | Luther et al. |
| 6,090,083 | A | 7/2000 | Sell et al. |
| 6,093,154 | A | 7/2000 | Burek et al. |
| 6,096,011 | A | 8/2000 | Trombley, III et al. |
| 6,099,519 | A | 8/2000 | Olsen et al. |
| 6,106,503 | A | 8/2000 | Pfeiderer et al. |
| 6,106,540 | A | 8/2000 | White et al. |
| 6,120,476 | A | 9/2000 | Fung et al. |
| 6,120,480 | A | 9/2000 | Zhang et al. |
| 6,132,407 | A | 10/2000 | Genese et al. |
| 6,142,981 | A | 11/2000 | Heck et al. |
| 6,155,610 | A | 12/2000 | Godeau et al. |
| 6,156,016 | A | 12/2000 | Maginot |
| 6,159,198 | A | 12/2000 | Gardeski et al. |
| 6,162,196 | A | 12/2000 | Hart et al. |
| 6,171,281 | B1 | 1/2001 | Zhang |
| 6,179,806 | B1 | 1/2001 | Sansoucy |
| 6,190,349 | B1 | 2/2001 | Ash et al. |
| 6,190,352 | B1 | 2/2001 | Haarala et al. |
| 6,190,371 | B1 | 2/2001 | Maginot et al. |
| 6,206,849 | B1 | 3/2001 | Martin et al. |
| 6,210,366 | B1 | 4/2001 | Sanfilippo, II |
| 6,213,988 | B1 | 4/2001 | McIvor et al. |
| 6,221,057 | B1 | 4/2001 | Schwartz et al. |
| 6,228,060 | B1 | 5/2001 | Howell |
| 6,228,062 | B1 | 5/2001 | Howell et al. |
| 6,258,058 | B1 | 7/2001 | Sanfilippo, II |
| 6,273,871 | B1 | 8/2001 | Davis et al. |
| 6,276,661 | B1 | 8/2001 | Laird |
| 6,293,927 | B1 | 9/2001 | McGuckin, Jr. |
| 6,322,541 | B2 | 11/2001 | West et al. |
| 6,331,176 | B1 | 12/2001 | Becker et al. |
| 6,332,874 | B1 | 12/2001 | Eliasen et al. |
| 6,338,725 | B1 | 1/2002 | Hermann et al. |
| 6,344,033 | B1 | 2/2002 | Jepson et al. |
| 6,352,520 | B1 | 3/2002 | Miyazaki et al. |
| 6,402,723 | B1 | 6/2002 | Lampropoulos et al. |
| 6,413,250 | B1 | 7/2002 | Smith et al. |
| 6,423,050 | B1 | 7/2002 | Twardowski |
| 6,423,053 | B1 | 7/2002 | Lee |
| 6,454,744 | B1 | 9/2002 | Spohn et al. |
| 6,458,103 | B1 | 10/2002 | Albert et al. |
| 6,494,860 | B2 | 12/2002 | Rocamora et al. |
| 6,497,681 | B1 | 12/2002 | Brenner |
| 6,508,790 | B1 | 1/2003 | Lawrence |
| 6,508,807 | B1 | 1/2003 | Peters |
| 6,520,939 | B2 | 2/2003 | Lafontaine |
| 6,544,247 | B1 | 4/2003 | Gardeski et al. |
| 6,551,283 | B1 | 4/2003 | Guo et al. |
| 6,562,023 | B1 * | 5/2003 | Marrs et al. ............ 604/533 |
| 6,575,960 | B2 | 6/2003 | Becker et al. |
| 6,589,262 | B1 | 7/2003 | Honebrink et al. |
| 6,592,544 | B1 | 7/2003 | Mooney et al. |
| 6,592,558 | B2 | 7/2003 | Quah et al. |
| 6,592,565 | B2 | 7/2003 | Twardowski |
| 6,623,460 | B1 | 9/2003 | Heck |
| 6,626,418 | B2 | 9/2003 | Kiehne et al. |
| 6,629,350 | B2 | 10/2003 | Motsenbocker |
| 6,632,200 | B2 | 10/2003 | Guo et al. |
| 6,638,242 | B2 | 10/2003 | Wilson et al. |
| 6,641,574 | B2 | 11/2003 | Badia Segura et al. |
| 6,645,178 | B1 | 11/2003 | Junker et al. |
| 6,663,595 | B2 | 12/2003 | Spohn et al. |
| 6,669,681 | B2 | 12/2003 | Jepson et al. |
| 6,682,498 | B2 | 1/2004 | Ross |
| 6,682,519 | B1 | 1/2004 | Schon |
| 6,689,109 | B2 | 2/2004 | Lynn |
| 6,692,464 | B2 | 2/2004 | Graf |
| 6,695,832 | B2 | 2/2004 | Schon et al. |
| 6,712,796 | B2 | 3/2004 | Fentis et al. |
| 6,719,749 | B1 | 4/2004 | Schweikert et al. |
| 6,722,705 | B2 | 4/2004 | Korkor |
| 6,827,710 | B1 | 12/2004 | Mooney et al. |
| 6,843,513 | B2 | 1/2005 | Guala |
| 6,872,198 | B1 | 3/2005 | Wilson et al. |
| 6,881,211 | B2 | 4/2005 | Schweikert et al. |
| D505,202 | S | 5/2005 | Chesnin |
| 6,887,220 | B2 | 5/2005 | Hogendijk |
| 6,893,056 | B2 | 5/2005 | Guala |
| 6,916,051 | B2 | 7/2005 | Fisher |
| 6,916,313 | B2 | 7/2005 | Cunningham |
| 6,921,396 | B1 | 7/2005 | Wilson et al. |
| 6,932,795 | B2 | 8/2005 | Lopez et al. |
| 6,969,381 | B2 | 11/2005 | Voorhees |
| 6,971,390 | B1 | 12/2005 | Vasek et al. |
| 7,044,441 | B2 | 5/2006 | Doyle |
| 7,048,724 | B2 | 5/2006 | Grossman et al. |
| 7,094,218 | B2 | 8/2006 | Rome et al. |
| 7,163,531 | B2 | 1/2007 | Seese et al. |
| 7,182,746 | B2 | 2/2007 | Haarala et al. |
| 7,258,685 | B2 * | 8/2007 | Kerr ............ 604/539 |
| 7,300,430 | B2 | 11/2007 | Wilson et al. |
| 7,347,853 | B2 | 3/2008 | DiFiore et al. |
| 7,377,915 | B2 | 5/2008 | Rasmussen et al. |
| 7,470,261 | B2 | 12/2008 | Lynn |
| 7,578,803 | B2 | 8/2009 | Rome et al. |
| 7,594,910 | B2 | 9/2009 | Butts et al. |
| 7,594,911 | B2 | 9/2009 | Powers et al. |
| 2001/0041857 | A1 | 11/2001 | Sansoucy |
| 2001/0041873 | A1 | 11/2001 | Dopper et al. |
| 2002/0010437 | A1 | 1/2002 | Lopez et al. |
| 2002/0077605 | A1 | 6/2002 | Fentis et al. |
| 2002/0099326 | A1 | 7/2002 | Wilson et al. |
| 2002/0099327 | A1 | 7/2002 | Wilson et al. |
| 2002/0128604 | A1 | 9/2002 | Nakajima |
| 2002/0147431 | A1 | 10/2002 | Lopez et al. |
| 2003/0065288 | A1 | 4/2003 | Brimhall et al. |
| 2003/0066218 | A1 | 4/2003 | Schweikert |
| 2003/0088213 | A1 | 5/2003 | Schweikert et al. |
| 2003/0153898 | A1 | 8/2003 | Schon et al. |
| 2003/0187411 | A1 | 10/2003 | Constantz |
| 2003/0199853 | A1 | 10/2003 | Olsen et al. |
| 2003/0201639 | A1 | 10/2003 | Korkor |
| 2003/0225379 | A1 | 12/2003 | Schaffer et al. |
| 2004/0065333 | A1 | 4/2004 | Wilson et al. |
| 2004/0082923 | A1 | 4/2004 | Field |
| 2004/0092863 | A1 | 5/2004 | Raulerson et al. |
| 2004/0097903 | A1 | 5/2004 | Raulerson |
| 2004/0122418 | A1 | 6/2004 | Voorhees |
| 2004/0158208 | A1 | 8/2004 | Hiejima |
| 2004/0167463 | A1 | 8/2004 | Zawacki et al. |
| 2004/0167478 | A1 | 8/2004 | Mooney et al. |
| 2004/0171997 | A1 | 9/2004 | Wilson et al. |
| 2004/0172003 | A1 | 9/2004 | Wilson et al. |
| 2004/0176739 | A1 | 9/2004 | Stephens et al. |
| 2004/0183305 | A1 | 9/2004 | Fisher |
| 2004/0186444 | A1 | 9/2004 | Daly et al. |
| 2004/0186445 | A1 | 9/2004 | Raulerson et al. |
| 2004/0193119 | A1 | 9/2004 | Canaud et al. |
| 2004/0243095 | A1 | 12/2004 | Nimkar et al. |
| 2005/0049555 | A1 | 3/2005 | Moorehead et al. |
| 2005/0080398 | A1 | 4/2005 | Markel et al. |
| 2005/0085765 | A1 | 4/2005 | Voorhees |
| 2005/0085794 | A1 | 4/2005 | Denoth et al. |
| 2005/0095891 | A1 | 5/2005 | Schorn |
| 2005/0096585 | A1 | 5/2005 | Schon et al. |
| 2005/0113805 | A1 | 5/2005 | Devellian et al. |
| 2005/0187535 | A1 | 8/2005 | Wilson et al. |
| 2005/0209572 | A1 | 9/2005 | Rome et al. |
| 2005/0209581 | A1 | 9/2005 | Butts et al. |
| 2005/0209584 | A1 | 9/2005 | Rome |
| 2005/0256461 | A1 | 11/2005 | DiFiore et al. |
| 2005/0261636 | A1 | 11/2005 | Rome et al. |
| 2005/0261664 | A1 | 11/2005 | Rome et al. |
| 2005/0261665 | A1 | 11/2005 | Voorhees |
| 2006/0015074 | A1 | 1/2006 | Lynn |
| 2006/0015086 | A1 | 1/2006 | Rasmussen et al. |
| 2006/0084929 | A1 | 4/2006 | Eliasen |
| 2006/0129134 | A1 | 6/2006 | Kerr |
| 2006/0276773 | A1 | 12/2006 | Wilson et al. |
| 2007/0016167 | A1 | 1/2007 | Smith et al. |

| | | | |
|---|---|---|---|
| 2007/0060866 | A1 | 3/2007 | Raulerson et al. |
| 2008/0009832 | A1 | 1/2008 | Barron et al. |
| 2008/0200901 | A1 | 8/2008 | Rasmussen et al. |
| 2009/0013944 | A1 | 1/2009 | Re Fiorentin et al. |
| 2009/0137944 | A1 | 5/2009 | Haarala et al. |
| 2010/0010445 | A1 | 1/2010 | Powers et al. |
| 2010/0016838 | A1 | 1/2010 | Butts et al. |

FOREIGN PATENT DOCUMENTS

| | | |
|---|---|---|
| EP | 0439263 A1 | 7/1991 |
| EP | 0616817 A1 | 9/1994 |
| WO | 8401902 A1 | 5/1984 |
| WO | 9722374 A1 | 6/1997 |
| WO | 0023137 A1 | 4/2000 |
| WO | 02058776 A2 | 8/2002 |
| WO | 03030960 A2 | 4/2003 |
| WO | 03030962 A2 | 4/2003 |
| WO | 03033049 A2 | 4/2003 |
| WO | 2006004943 A2 | 1/2006 |
| WO | 2006066023 A2 | 6/2006 |
| WO | 2006130133 A1 | 12/2006 |

OTHER PUBLICATIONS

CAMP, "Care of the Groshong Catheter", Oncol Nurs Forum, vol. 15, No. 6, 1988.

Delmore et al, "Experience with the Groshong Long-Term Central Venous Catheter", Gynecologic Oncology 34, 216-218 (1989).

Goldfarb et al., "Chronic Venous Access Bedside Placement Technique and Complications," Cancer Practice vol. 2, No. 4, pp. 279-283 (Jul./Aug. 1994).

Health Devices, "Hazard Report," vol. 25, Nos. 5-6, pp. 214-215, May-Jun. 1996.

Hull et al., "The Groshong Catheter: Initial Experience and Early Results of Imging-guided Placement," Cardiovascular Radiology 185:803-807 (1992).

Malviya et al., "Vascular Access in Gynecological Cancer Using the Groshong Right Atrial Catheter", Gynecological Oncology 33, 313-316 (1989).

PCT/US2005/009150 filed Mar. 18, 2005 Preliminary Report on Patentability dated May 26, 2006.

PCT/US2005/009150 filed Mar. 18, 2005 Search Report dated Jun. 7, 2005.

PCT/US2005/009150 filed Mar. 18, 2005 Written Opinion dated Jun. 17, 2005.

PCT/US2010/040084 filed Jun. 25, 2010 Search Report dated Sep. 27, 2010.

PCT/US2010/040084 filed Jun. 25, 2010 Written Opinion dated Sep. 27, 2010.

Salem et al., "A New Peripherally Implanted Subcutaneous Permanent Central Venous Access Device for Patients Requiring Chemotherapy," Journal of Clinical Oncology, vol. 11, No. 11, p. 2181-2185 (Nov. 1993).

Twardowski et al., "Measuring Central Venous Structures in Humans: Implications for Central-Vein Catheter Dimensions," The Journal of Vascular Access 3:21-37 (2002).

U.S. Appl. No. 10/803,207, filed Mar. 18, 2004 Non-Final Office Action dated Sep. 19, 2005.

U.S. Appl. No. 10/803,207, filed Mar. 18, 2004 Notice of Allowance dated Apr. 21, 2006.

U.S. Appl. No. 10/803,279, filed Mar. 18, 2004 Advisory Action dated Aug. 22, 2007.

U.S. Appl. No. 10/803,279, filed Mar. 18, 2004 Final Office Action dated May 31, 2007.

U.S. Appl. No. 10/803,279, filed Mar. 18, 2004 Final Office Action dated Oct. 1, 2008.

U.S. Appl. No. 10/803,279, filed Mar. 18, 2004 Non-Final Office Action dated Apr. 2, 2009.

U.S. Appl. No. 10/803,279, filed Mar. 18, 2004 Non-Final Office Action dated Jun. 5, 2006.

U.S. Appl. No. 10/803,279, filed Mar. 18, 2004 Non-Final Office Action dated Sep. 20, 2007.

U.S. Appl. No. 10/803,279, filed Mar. 18, 2004 Non-Final Office Action dated Dec. 1, 2006.

U.S. Appl. No. 10/803,279, filed Mar. 18, 2004 Notice of Allowance dated May 28, 2009.

U.S. Appl. No. 10/803,512, filed Mar. 18, 2004 Advisory Action dated Oct. 16, 2008.

U.S. Appl. No. 10/803,512, filed Mar. 18, 2004 Final Office Action dated May 30, 2008.

U.S. Appl. No. 10/803,512, filed Mar. 18, 2004 Non-Final Office Action dated Jan. 24, 2008.

U.S. Appl. No. 10/803,512, filed Mar. 18, 2004 Non-Final Office Action dated May 24, 2010.

U.S. Appl. No. 10/803,512, filed Mar. 18, 2004 Non-Final Office Action dated Jul. 22, 2009.

U.S. Appl. No. 10/803,512, filed Mar. 18, 2004 Final Office Action dated Sep. 28, 2010.

U.S. Appl. No. 10/803,513, filed Mar. 18, 2004 Non-Final Office Action dated Jul. 25, 2008.

U.S. Appl. No. 10/803,513, filed Mar. 18, 2004 Notice of Allowance dated Jun. 12, 2009.

U.S. Appl. No. 11/076,564, filed Mar. 8, 2005 Advisory Action dated Nov. 16, 2006.

U.S. Appl. No. 11/076,564, filed Mar. 8, 2005 Final Office Action dated Jul. 27, 2007.

U.S. Appl. No. 11/076,564, filed Mar. 8, 2005 Final Office Action dated Aug. 25, 2006.

U.S. Appl. No. 11/076,564, filed Mar. 8, 2005 Non-Final Office Action dated Jan. 23, 2008.

U.S. Appl. No. 11/076,564, filed Mar. 8, 2005 Non-Final Office Action dated Feb. 9, 2007.

U.S. Appl. No. 11/076,564, filed Mar. 8, 2005 Non-Final Office Action dated Mar. 9, 2006.

U.S. Appl. No. 11/076,564, filed Mar. 8, 2005 Non-Final Office Action dated Dec. 17, 2008.

U.S. Appl. No. 11/076,564, filed Mar. 8, 2005 Notice of Allowance dated Jun. 17, 2009.

U.S. Appl. No. 11/096,553, filed Apr. 1, 2005 Advisory Action dated Aug. 1, 2007.

U.S. Appl. No. 11/096,553, filed Apr. 1, 2005 Final Office Action dated Feb. 27, 2007.

U.S. Appl. No. 11/096,553, filed Apr. 1, 2005 Non-Final Office Action dated Jan. 24, 2006.

U.S. Appl. No. 11/096,553, filed Apr. 1, 2005 Non-Final Office Action dated May 19, 2006.

U.S. Appl. No. 11/096,553, filed Apr. 1, 2005 Non-Final Office Action dated Oct. 10, 2007.

U.S. Appl. No. 11/096,553, filed Apr. 1, 2005 Notice of Allowance dated Mar. 25, 2008.

U.S. Appl. No. 11/122,303, filed May 3, 2005 Advisory Action dated Jul. 14, 2008.

U.S. Appl. No. 11/122,303, filed May 3, 2005 Final Office Action dated Apr. 30, 2008.

U.S. Appl. No. 11/122,303, filed May 3, 2005 Non-Final Office Action dated Jan. 20, 2010.

U.S. Appl. No. 11/122,303, filed May 3, 2005 Non-Final Office Action dated Jun. 8, 2009.

U.S. Appl. No. 11/122,303, filed May 3, 2005 Non-Final Office Action dated Sep. 13, 2007.

U.S. Appl. No. 11/122,303, filed May 3, 2005 Notice of Allowance dated Jul. 9, 2010.

U.S. Appl. No. 11/122,303, filed May 3, 2005 Notice of Allowance dated Sep. 2, 2010.

U.S. Appl. No. 11/471,193, filed Jun. 20, 2006 Non-Final Office Action dated Jan. 14, 2010.

U.S. Appl. No. 11/471,193, filed Jun. 20, 2006 Notice of Allowance dated Jul. 26, 2010.

U.S. Appl. No. 12/106,704, filed Apr. 21, 2008 Final Office Action dated Apr. 15, 2010.

U.S. Appl. No. 12/106,704, filed Apr. 21, 2008 Non-Final Office Action dated Apr. 27, 2009.

U.S. Appl. No. 12/106,704, filed Apr. 21, 2008 Non-Final Office Action dated Oct. 22, 2009.

U.S. Appl. No. 12/563,776, filed Sep. 21, 2009 Non-Final Office Action dated Jun. 16, 2010.
U.S. Appl. No. 12/563,776, filed Sep. 12, 2009 Notice of Allowance dated Nov. 12, 2010.
U.S. Appl. No. 12/563,996, filed Sep. 21, 2009 Final Office Action dated Dec. 1, 2011.
U.S. Appl. No. 12/563,996, filed Sep. 21, 2009 Non-Final Office Action dated Jun. 13, 2011.
Vesely, "Central Venous Catheter Tip Position: A Continuing Controversy," JVIR vol. 14, No. 5, pp. 527-534 (May 2003).

* cited by examiner

CONNECTION SYSTEM FOR MULTI-LUMEN CATHETER

PRIORITY

This application is a division of U.S. patent application Ser. No. 11/471,193, filed Jun. 20, 2006, now U.S. Pat. No. 7,875, 019, which claims the benefit, under 35 U.S.C. §119(e), to U.S. Provisional Patent Application No. 60/692,180, filed Jun. 20, 2005, each of which is incorporated by reference in its entirety into this application as if fully set forth herein.

BRIEF SUMMARY

Optimal placement of certain multi-lumen catheters involves the use of a reverse tunnel technique in order to accurately position the distal tip of the catheter within the desired location in a patient's blood vessel and to facilitate positioning of the proximal portion of the catheter within a subcutaneous tunnel. Different from a multi-lumen catheter including an integral proximal connection system (for connection to an extracorporeal device), a multi-lumen catheter for placement via reverse tunneling generally includes an open proximal end, meaning that a connection system for use therewith is attachable following the tunneling procedure. It is therefore desirable to provide a connection system for an open ended multi-lumen catheter that has been reverse tunneled or otherwise placed within a patient's body. In many instances, it is desirable that this connection system provide an irreversible connection with the catheter in order to avoid unintentional disconnection, and also provide a fluid tight connection with the catheter to prevent leaking.

Accordingly, a connection system for a multi-lumen catheter is described herein, the connection system providing a connection between a medical device configured for insertion into the body of a patient (e.g., a catheter) and extracorporeal equipment (e.g., extension tubing). In one embodiment, the connection system provides an irreversible connection between a catheter and a hub assembly, such as a bifurcation assembly with extension tubing. In one embodiment, the hub assembly includes a collet with a threaded outer surface configured to establish a locking relationship with a collar. The collar may initially be independent from the collar and positioned over a proximal end of a catheter shaft. The hub assembly may include one or more cannulae for insertion into the lumen(s) of the catheter shaft. After the catheter shaft is pushed over the cannula(s), the collar is brought into locking relationship with the collet by threading thereover.

In one embodiment, once the locking relationship has been established between the collet and the collar, the collar is freely rotatable about the collet and catheter shaft. In one aspect, the collet includes an inner barbed or ridged surface such that once the locking relationship has been established, the barbed or ridged surface presses into the catheter shaft, causing material creep to take place into the voids between adjacent barbs or ridges. This phenomenon further strengthens the locking connection, preventing accidental disconnection of the hub assembly from the catheter shaft as the forces required to disconnect the components is well above that which could normally be expected.

In one embodiment, a connection system for a catheter includes a hub assembly, including a cannula configured for insertion into a lumen of a catheter, a collet connected to the hub assembly and positioned about a distal portion of the cannula, an inner surface of the collet spaced from the cannula to permit passage of a catheter wall between the collet and the cannula, the collet including a barb on an outer surface thereof, and a collar including an attachment barb configured to engage the collet barb. In one embodiment, a method of connecting a catheter to a hub assembly, includes inserting a lumen of a catheter through a collet lumen and over a hub assembly cannula, engaging a portion of the collet with a collar, and moving the collar over the collet such that respective attachment barbs on the collet and collar are engaged.

Also disclosed herein is a multifunction adaptor for use with an open-ended catheter shaft prior to connection to a hub assembly. In one embodiment, the multifunction adaptor includes a C-clip for creating a locking connection with a tunneler instrument, a valve to prevent fluid loss as the catheter is being placed, and a retention ring. The multifunction adaptor is configured to be inserted into the proximal end of a catheter shaft. In one embodiment, the catheter shaft of a multi-lumen catheter includes a proximal portion without a septum or dividing wall to receive a distal end of the multifunction adaptor. The proximal end of the multifunction adaptor, in addition to being configured to receive a distal end of a tunneler instrument, is also configured to receive an end of a syringe so that the catheter shaft may be flushed prior to connection to the hub assembly.

In one embodiment, a multifunction adaptor includes a housing including an inner lumen extending therethrough and a distal end configured for insertion into the lumen of a catheter shaft, a retention member positioned in the inner lumen at a proximal position of the housing, the retention member including an opening sized to permit insertion of a tunneler tip therethrough, a valve positioned in the inner lumen of the housing, including an opening to permit passage of a guidewire, and a retention ring positioned in the inner lumen of the housing distal of the valve. In another embodiment, a multifunction adaptor includes a housing including an inner lumen extending therethrough, a retention member positioned in the inner lumen at a proximal position of the housing, the retention member including an opening sized to permit insertion of a tunneler tip therethrough, a valve positioned in the inner lumen of the housing, the valve including an opening to permit passage of a guidewire, and a nose cone tube, a first portion thereof positioned within a distal portion of the housing inner lumen, a second portion thereof extending outside of the housing and being configured for insertion within a catheter shaft.

These and other embodiments, features and advantages of the present invention will become more apparent to those skilled in the art when taken with reference to the following more detailed description of the invention in conjunction with the accompanying drawings that are first briefly described.

DETAILED DESCRIPTION

Figure 1A:
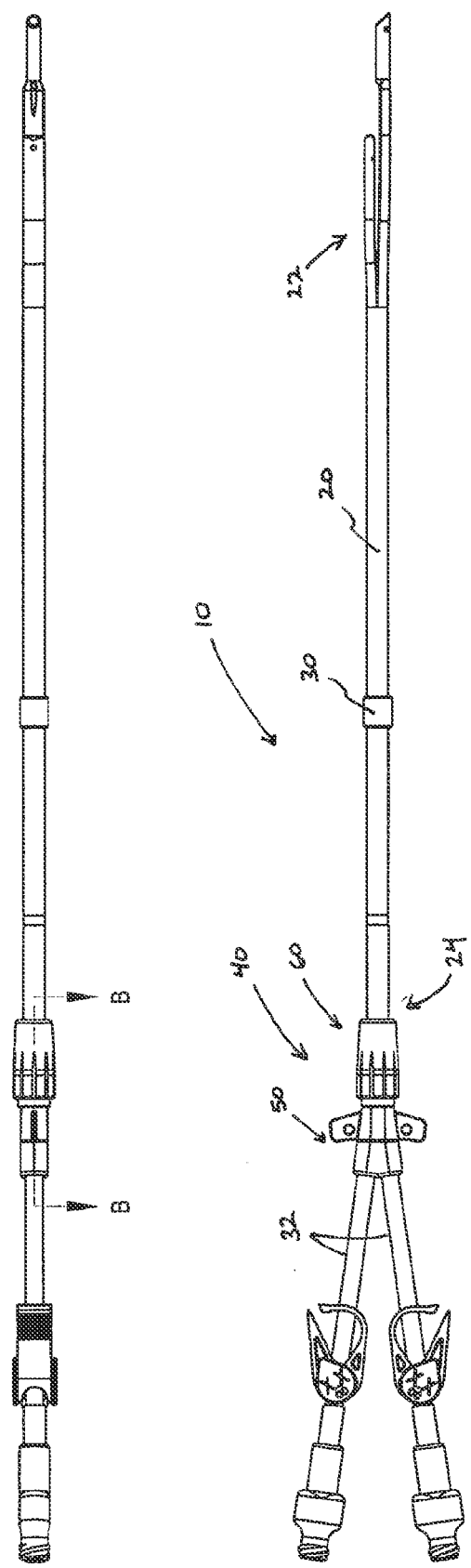
FIG. 1A is both a side and top view of one embodiment of an assembled multi-lumen catheter with a connection system.

The following detailed description should be read with reference to the drawings. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives, and uses of the invention, including what is presently believed to be the best mode of carrying out the invention.

The examples and illustrations of a connection system for a multi-lumen catheter are described herein with respect to connection of a dual lumen catheter to a bifurcation assembly. However, the inventive connection system is equally applicable for use with a single lumen catheter or a catheter including more than two lumens and thus is not limited to the number of lumens in the catheter. Moreover, while certain materials are discussed herein with respect to the components of a catheter, connection system, adaptor, etc., the connection system is not limited to such materials. The term "hub assembly" as used herein means any device that is utilized to connect the lumen or lumens of a catheter to an extracorporeal system, such as a dialysis machine, including a bifurcation assembly. The term "collet" as used herein means any member connected to the hub assembly, including surfaces or mechanisms configured to mate with or engage a collar. The term "collar" as used herein means any member independent of the hub assembly, including surfaces or mechanisms configured to mate with or engage a collet.

In one embodiment of a connection system for a multi-lumen catheter, a one time, irreversible connection between a dual lumen catheter shaft and two cannulae contained in a bifurcation assembly is provided. The irreversible aspect of the system pertains to the locking connection between a collar and a collet attached to the bifurcation assembly, as well as the "creep" properties of catheter shaft material. More particularly, in the case that the catheter shaft to be connected to the bifurcation assembly is comprised of polyurethane, silicone or like material (e.g., a low durometer plastic or elastomer), the configuration of the inner surface of the collet, which includes barbs or ridges and therefore voids between adjacent barbs or ridges, and the fact that the inner surface of the collet is pressed into the catheter shaft as the collar engages the collet, results in material of the catheter shaft flowing into the voids over time. This movement of material of the catheter shaft into the voids of the collet inner surface results in a strengthened connection between the catheter and bifurcation assembly. Thus, the incorporation of the barbs or ridges in the collet provides enhanced mechanical fixation of the catheter shaft.

In one embodiment of a connection system for a multi-lumen catheter, a collet is attached to a hub assembly, the collet including several barbs or ridges on an inner surface thereof. The length of the collet is sufficient to provide a barbed surface with which a catheter or tube is gripped even if the catheter or tube is not fully inserted into the connection system. Such a feature mitigates the severity of user error by maintaining connectivity between the catheter or tube and hub assembly. One potential feature of a connection system is a release mechanism to permit a collar of the connection system to freely rotate about the catheter shaft once the connection between the catheter and hub assembly has been established. In one embodiment incorporating a release mechanism, an audible or tactile indication signals to the user that a connection between, for example, a collar and collet has been established (e.g., a snap lock is provided after the collar has been fully threaded over the collet). A thread assembly on the collar and collet allows the two components to rotate freely with respect to one another, providing a feature for patient comfort. The thread assembly in one embodiment is a one-time connection which prevents accidental detachment by the user. In one aspect of a connection system, a compression nut or collar includes a compression ring (e.g., a cylindrical piece of pliable material, such as silicone, disposed on the inner surface thereof). The compression ring seals against the catheter or tube over which the collar is positioned when the collar is connected to the hub assembly and in combination with the barbs or ridges on the collet provides enhanced load-bearing capability and improved sealing against pressures.

Another potential feature of a connection system is the fashioning of the lumens of a catheter to correspond to the shape of the cannulae of a hub assembly. In one embodiment, the cross-sectional shape of the lumens are similar to the cross-sectional shape of the cannulae, but are sized slightly smaller such that a compression fit is created when the cannulae are inserted into the lumens. Such a design reduces fluid loss between the hub assembly and catheter. Also, the compression fit between the cannulae and catheter lumens is enhanced in one embodiment by providing convex surfaces on each. For example, in one embodiment, the cross-sectional shape of both the cannulae and catheter lumens resemble an eye, including curved upper and lower portions that converge to a point at both sides. Another potential feature is a collar that includes a compression member such that upon attachment of the collar to the hub assembly, a compression field is created around the catheter shaft and cannulae inserted therein.

Figure 1B:
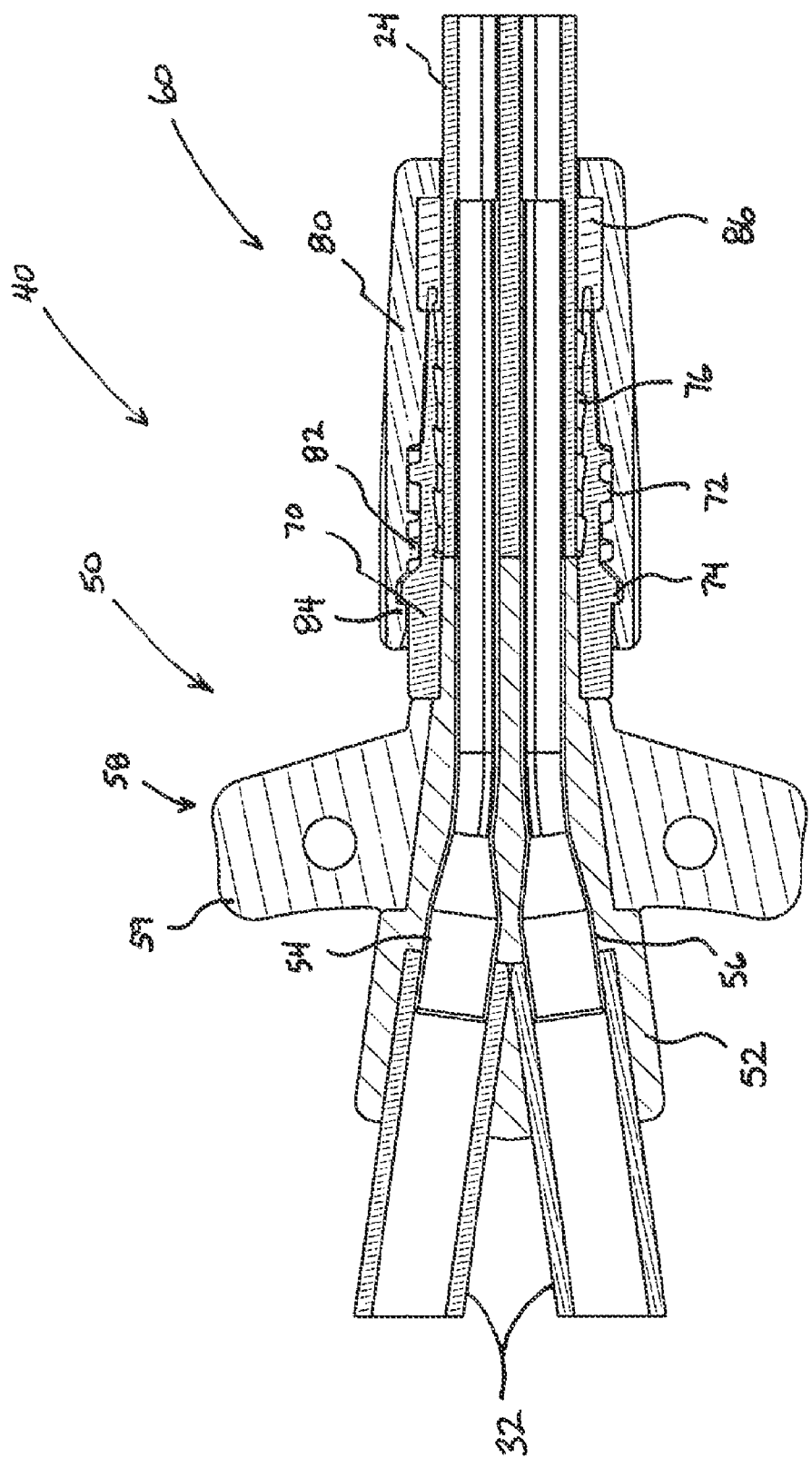
FIG. 1B is a cross-sectional view, taken along the line B-B, of the connection system shown in FIG. 1A.

Referring now to FIG. 1A, a catheter assembly 10 is shown, including a catheter shaft 20. The catheter shaft 20 has a distal end 22 in a split-tip configuration, as described in U.S. Patent Application Publication No. 2004/0167463 ("Multi-Lumen Catheter with Separate Distal Tips"), published Aug. 26, 2004, which is expressly incorporated by reference as if fully set forth herein. It should be appreciated, however, that the connection system described herein is not limited to any particular type of multi-lumen catheter shaft. The assembly 10 includes a cuff 30 disposed about the catheter shaft 20, a connection system 40 connected to a proximal end 24 of the catheter shaft, and a pair of extension legs 32 attached to the connection system 40, which includes a includes a hub assembly 50 and a connector assembly 60. FIG. 1B illustrates a cross-sectional view along section A-A of FIG. 1A, showing several aspects of the connection system 40.

The hub assembly 50 includes a core member 52, through which a first and second cannulae 54, 56 are insert molded or otherwise connected to, associated with, or inserted through. The cannulae 54, 56 extend distally of the core member 52 to provide a length over which a multi-lumen catheter shaft may be positioned and in one embodiment may include metal (e.g., titanium, etc.). Around the proximal end of the cannulae 54, 56, extension legs 32 are positioned, which are essentially tubes or conduits that are in fluid communication with the catheter lumens following connection of the catheter shaft to the hub assembly. A bifurcation 58 can be overmolded over only a mid region of the core member 52 as shown, or a more substantial portion thereof (FIG. 3C). In FIG. 1B, the core member 52 includes proximal openings for insertion of the extension legs 32, which have distal ends surrounding proximal ends of the cannulae 54, 56 in a substantially fluid tight arrangement. The bifurcation 58, including a pair of wings 59 with suture holes therein, is overmolded over a mid region of the core member 52 to provide a soft interface for the patient. In one embodiment, the core member 52 includes polyurethane (Shore D) and the bifurcation 58 includes polyurethane (Shore A).

The connector assembly 60 includes a barbed collet 70 that is attached (e.g., by solvent bonding) to the distal end of the core member 52 such that the collet is circumferentially disposed about a distal portion of the cannulae 54, 56 and spaced apart therefrom. The barbed collet 70 has a threaded tapered surface, including threads 72, on an exterior thereof and a barbed or ridged surface, including ridges 76, on an interior thereof. The external threads 72 are configured to interact with threads 82 of similar shape and depth on an internal threaded surface of a compression nut or collar 80 during attachment of the collar 80 to the collet 70. The collet 70 also includes at a proximal end an attachment barb 74 on an outer surface thereof to engage the attachment barb 84 on an inner surface of the compression collar 80. The barbs 74, 84 in the embodiment shown are essentially respective raised circumferential sections with shoulders 73, 83 (FIG. 1D) that are in abutting relation when the collar 80 is connected to the collet 70. To connect, the collar 80 is moved/rotated over the collet 70 until the collar barb 84 passes over the collet barb 74, which action provides an audible or tactile indication to the user. Because the cross-sectional size and shape of the collet barb 74 of the collet 70 is substantially the same as that of the recess adjacent the barb 84 on an inner surface of the collar 80, rotation of the collar 80 after connection to the collet 70 is permitted. It should be appreciated that the described configuration for the attachment barbs 74, 84 for engagement between the collet 70 and collar 80 is exemplary and that other embodiments may include different sizes, shapes and/or arrangements.

Figure 1C:
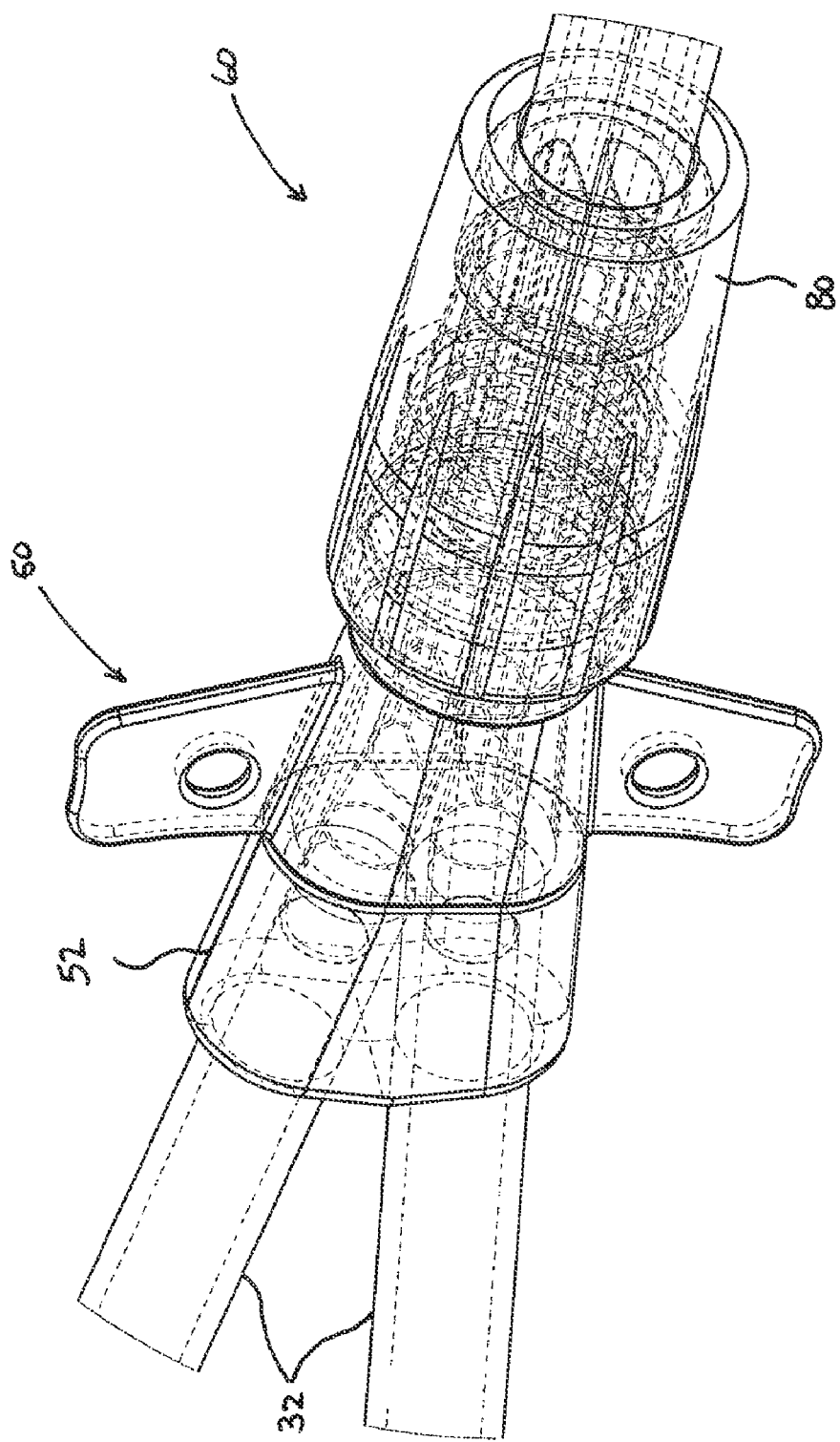
FIG. 1C is a transparent view of a depiction of the hub assembly and connection system of FIG. 1A without the catheter being attached.
Figure 1D:
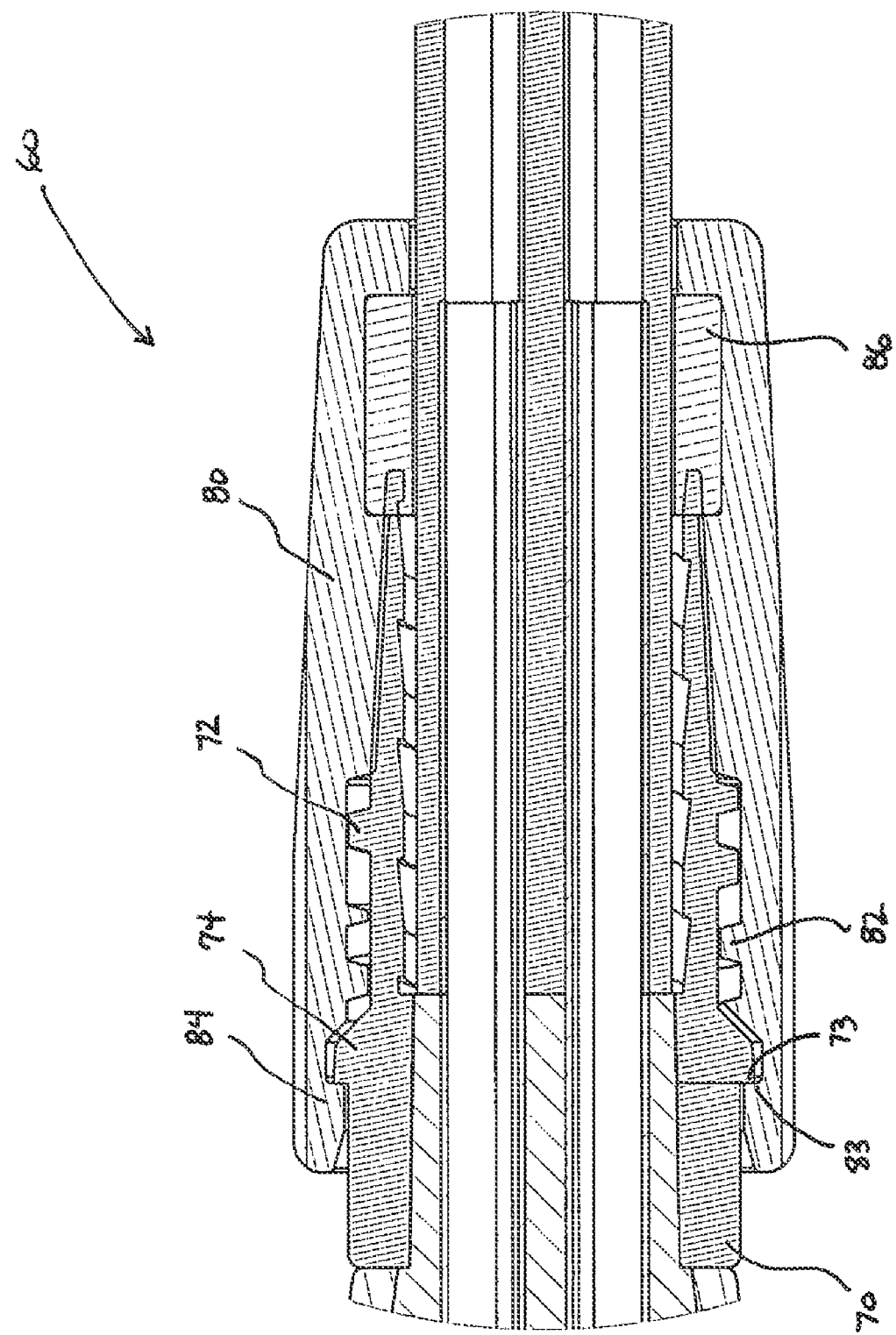
FIG. 1D is an enlarged cross-sectional view of FIG. 1B, showing particularly the interaction between the collet and collar of the connector assembly.

As discussed, a permanent connection between the collet 70 and collar 80 is verified upon engagement of the respective attachment barbs 74, 84 by an audible or tactile indication, which engagement permits free rotation of the collar 80 about the collet 70. The collar 80 in this embodiment, in addition to the internal threaded tapered surface to interact with the outer threaded tapered surface of the collet and the internal attachment barb 84 to interact with the outer attachment barb 74 of the collet, includes a compression ring 86 positioned along a distal inner surface thereof, which compresses against the catheter shaft when the collar 80 is connected to the hub assembly 50. FIG. 1C is a transparent view of the hub assembly 50 and connector assembly 60 of FIGS. 1A and 1B in the fully assembled position without the catheter shaft 20 attached. FIG. 1D is an enlarged view of the collar 80 and collet 70 of FIG. 1B after a connection therebetween has been established. From this view, the threads 72 of collet 70 can be seen spaced from the threads 82 of the collar 80 and the barbs 74, 84, and shoulders 73, 83 thereof can be seen in greater detail.

Figure 2A:
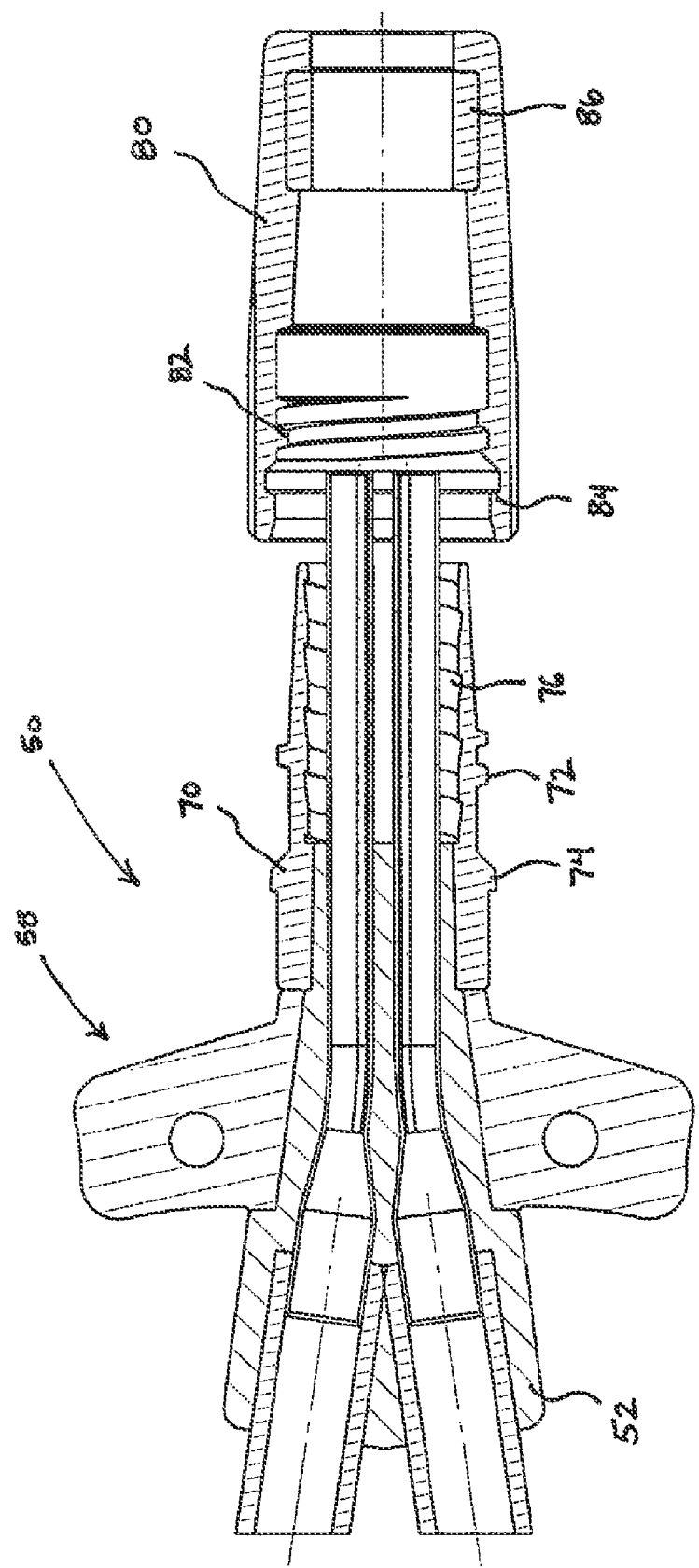
FIG. 2A is a longitudinal cross-sectional view of a connection system prior to connection between a collar and collet.
Figure 2B:
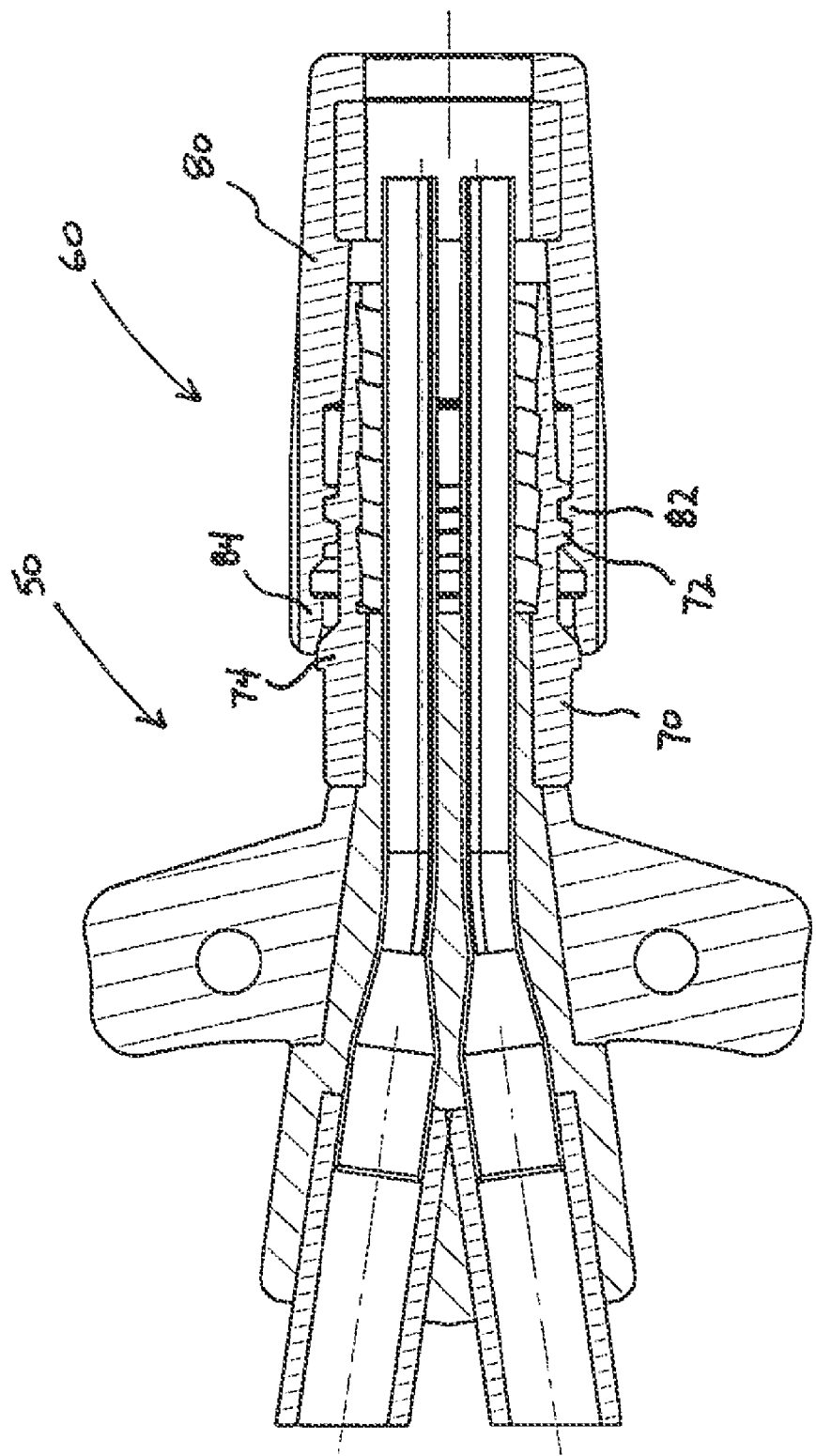
FIG. 2B is a longitudinal cross-sectional view the connection system during connection, showing engagement of threads.
Figure 2C:
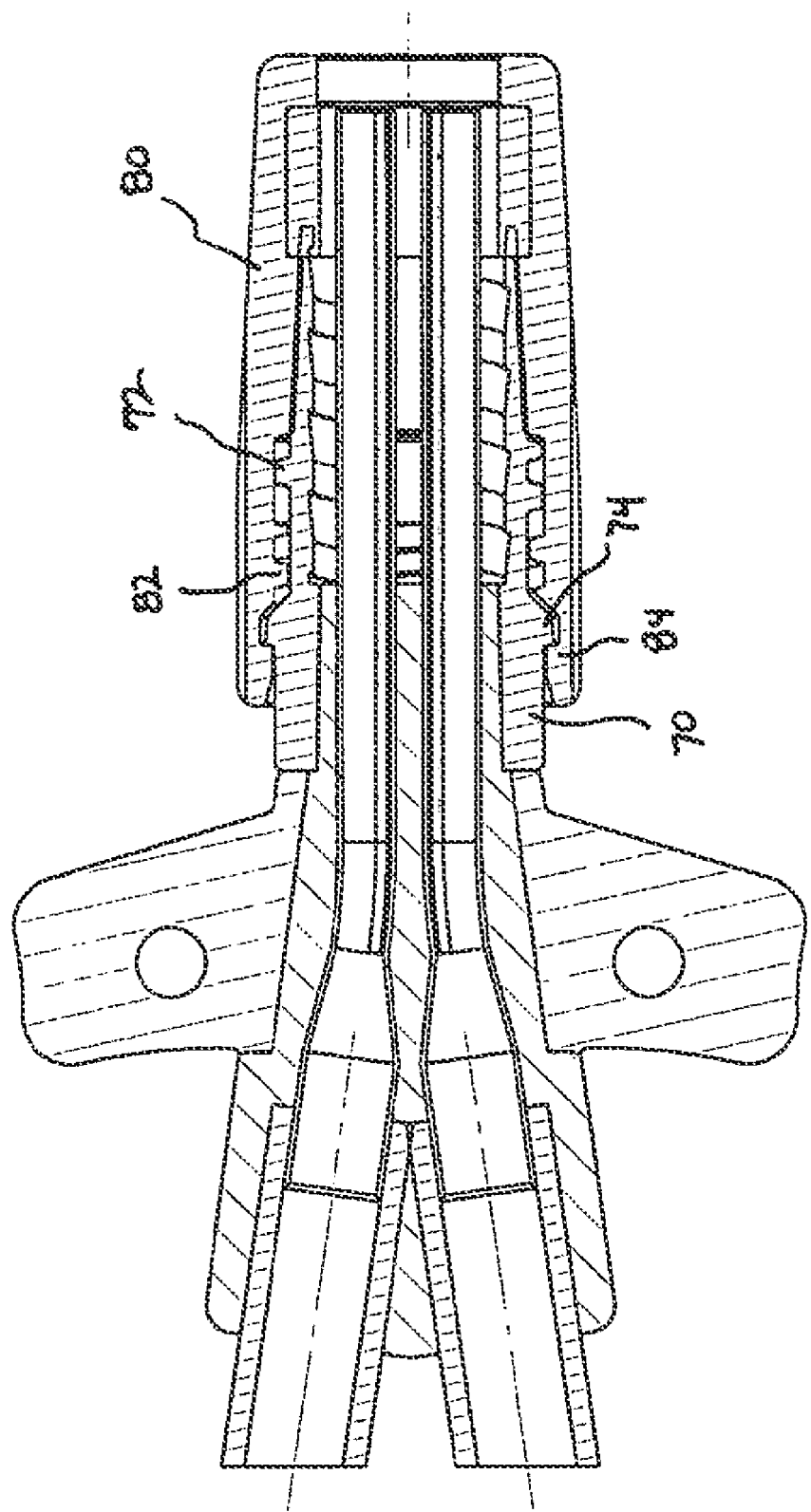
FIG. 2C is a longitudinal cross-sectional view of the connection system following connection, showing engagement of attachment barbs.

FIGS. 2A-2C illustrate three steps for connecting the collar 80 to the collet 70. Although not shown here, it should be appreciated that the initial step in connecting an open-ended multi-lumen catheter shaft to hub assembly 50 as described is to insert the proximal end of the catheter shaft through the interior of the collet 70 and into abutting relation with the core member 52 by inserting the cannulae 54, 56 into the lumens of the catheter shaft, as shown in FIG. 1B such that an outer catheter wall passes between the collet 70 and the cannulae 54, 56. The inner barbs or ridges 76 of the collet 70 act to hold the catheter shaft in place while the collar 80 is moved in a proximal direction toward the hub assembly 50 and into locking position with respect to the collet 70 (it should be appreciated that for illustration purposes, the figures herein do not show the ridges 76 pressed into the catheter shaft 20). FIG. 2A shows the collar 80 prior to engagement with the collet 70, illustrating the configuration of each. The collet 70 includes on its outer surface an attachment barb 74 at a proximal end, threads 72 and a distal tapered surface to interact and/or mate with the attachment barb 84, threads 82 and distal tapered surface on the inner surface of the collar 80.

FIG. 2B illustrates an engagement of the respective threads 82, 72 of the collar 80 and collet 70, prior to engagement of the attachment barbs 84, 74, as the collar 80 is moved in a proximal direction over the collet 70. Rotation of the collar 80 drives it further onto the collet 70, increasing the contact between the respective tapered surfaces thereof and radially compressing the collet 70 such that the inner barbs or ridges 76 engage the outer surface of the catheter shaft. The compression of the inner barbs or ridges 76 of the collet 70 onto the catheter shaft drives the "creep" of the catheter shaft material as discussed above. FIG. 2C shows the full engagement of the collar 80 and collet 70, such that the attachment barbs 84, 74 are engaged, but the threads 72 of the collet 70 are offset from the threads 82 of the collar 80 such that they are disengaged, which permits free rotation of the collar 80 about the collet 70. In this position, the respective threads 72, 82 cannot be re-engaged. As mentioned above, an audible or tactile indication provides the user with verification that engagement of the attachment barbs 74, 84 has been established.

Figure 3A:
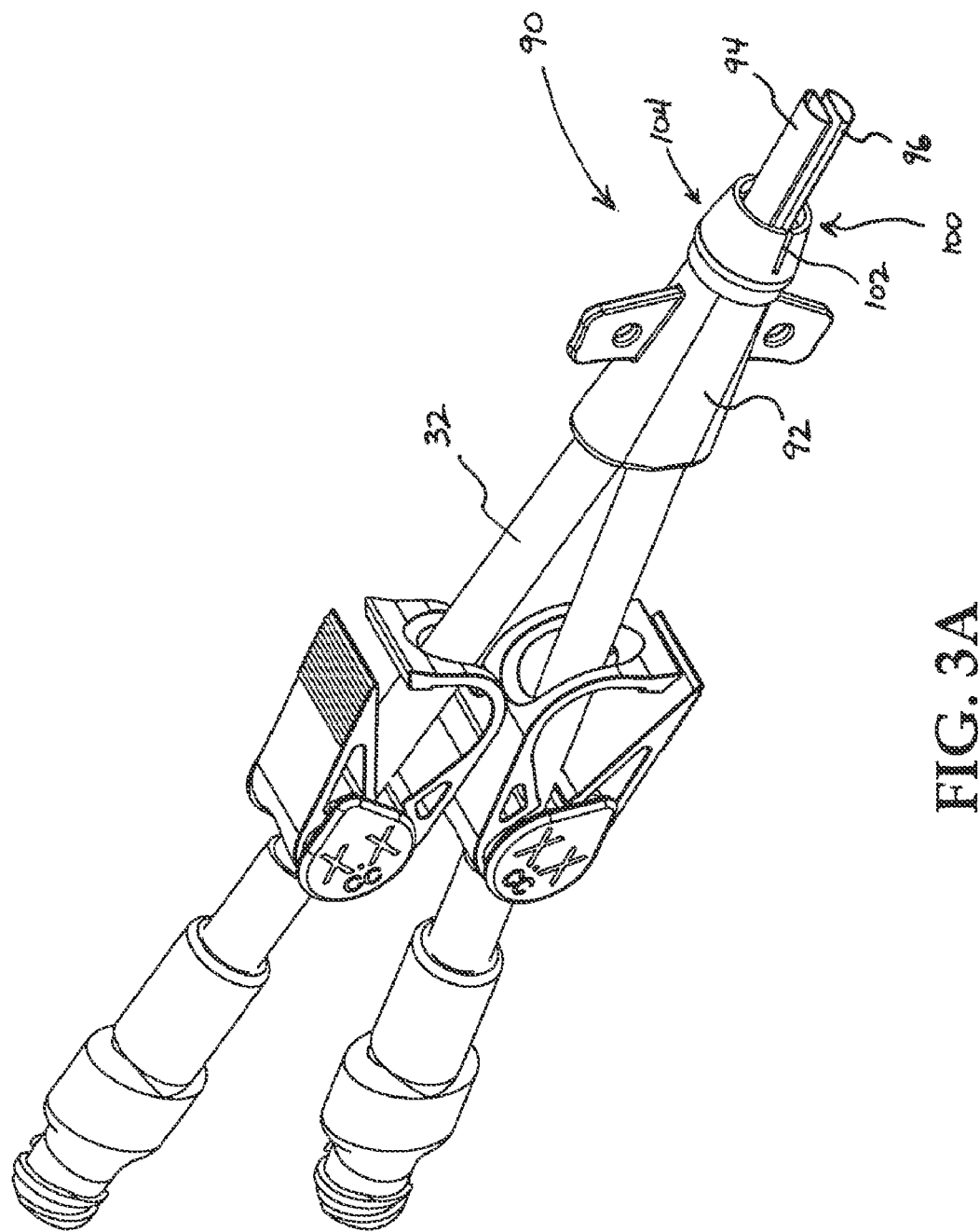
FIG. 3A is a perspective view of another embodiment of a connection system.
Figure 3B:
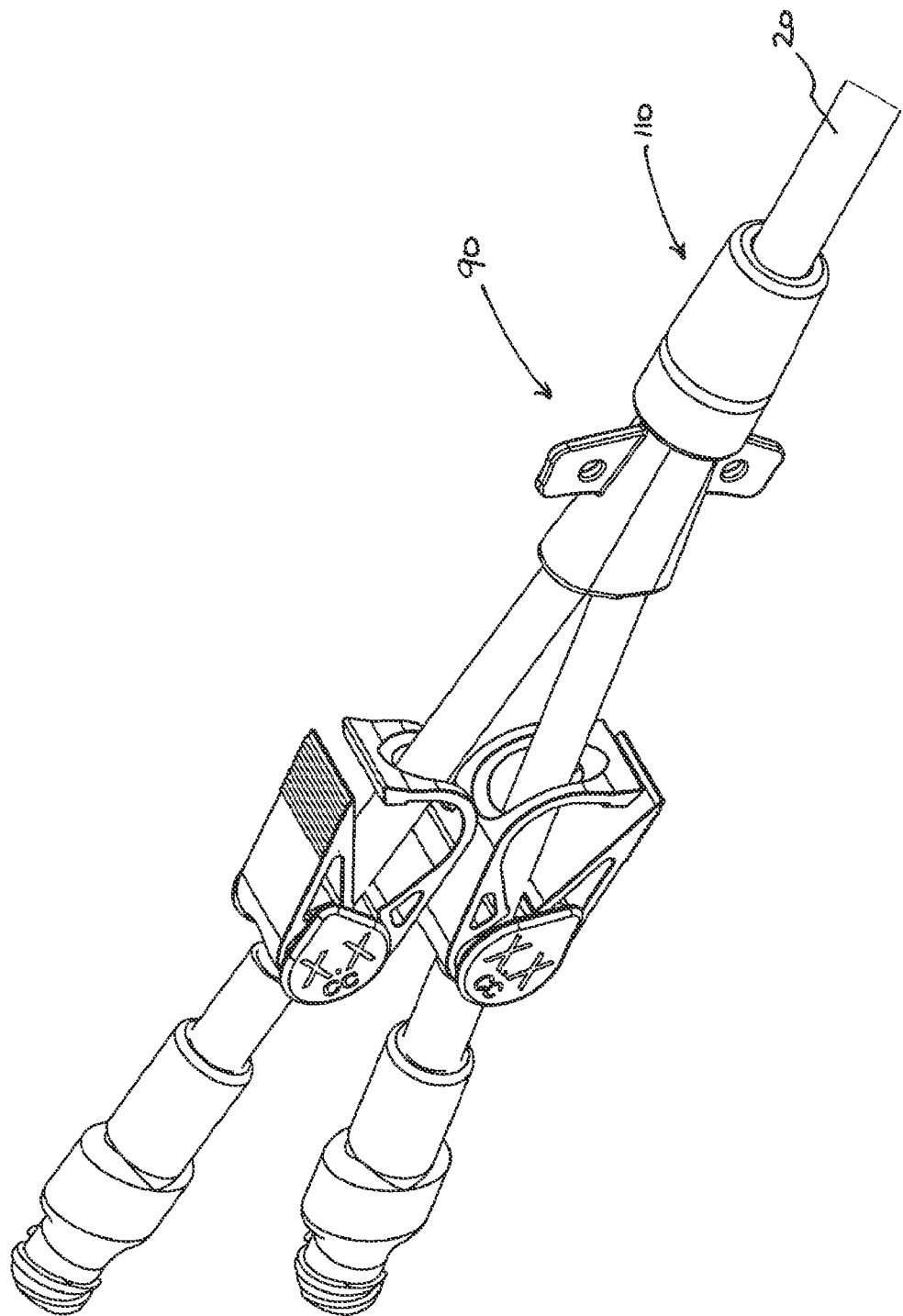
FIG. 3B is a perspective view of the connection system of FIG. 3A shown attaching a catheter to a hub assembly.
Figure 3C:
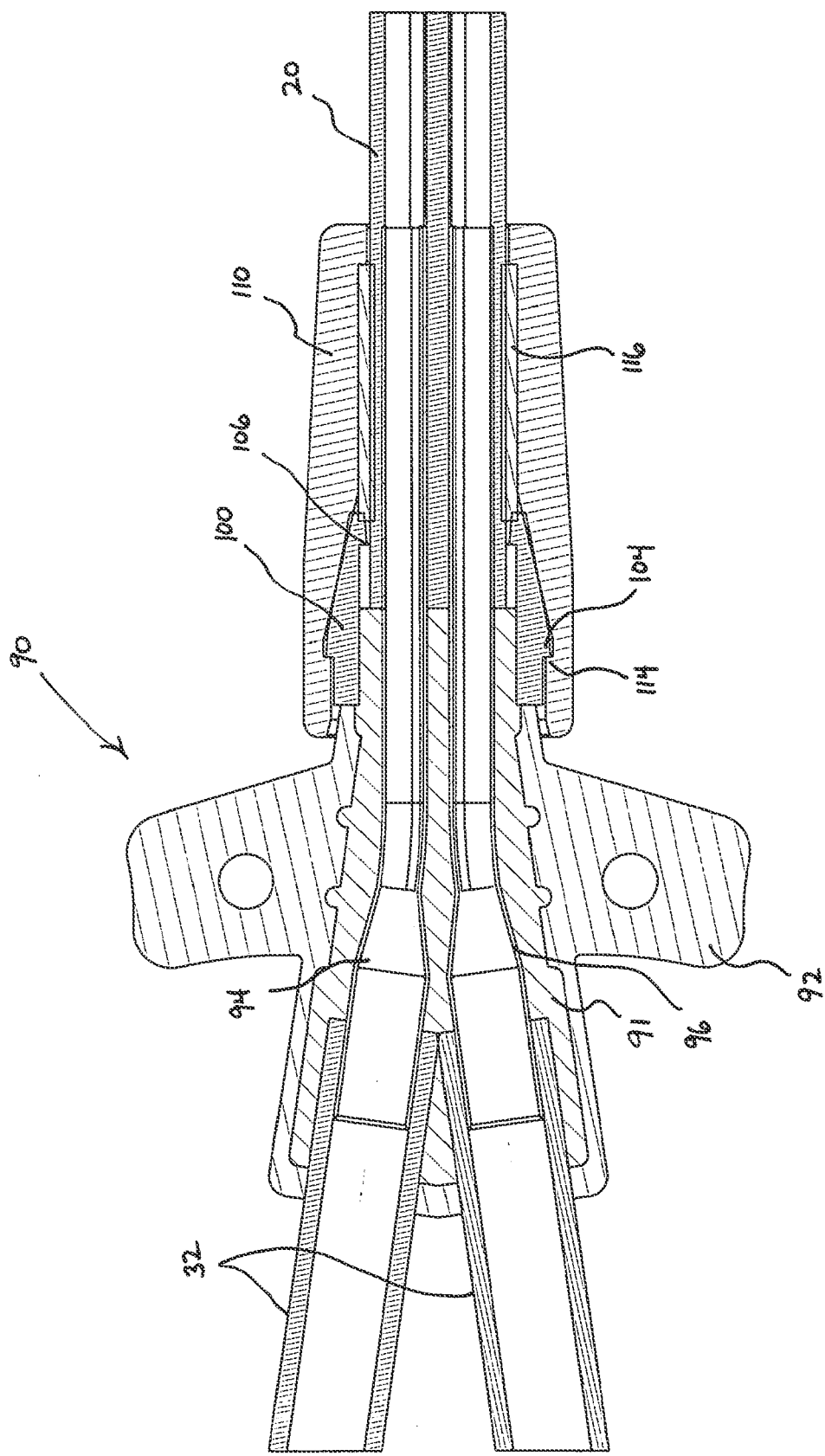
FIG. 3C is a longitudinal cross-sectional view of FIG. 3B, showing the interconnection between components.

FIGS. 3A-3C illustrate another embodiment of a multi-lumen catheter connector. In FIG. 3A, a hub assembly 90 is shown, similar to that of FIGS. 1-2. A bifurcation 92 is overmolded about a core member 91, which includes a ribbed outer surface to facilitate bonding of the bifurcation 92. A pair of cannulae 94, 96 are disposed through the core member 91 and may be bonded (e.g., solvent, adhesive, etc.) thereto. The extension legs 32 are positioned over the proximal end of the cannulae 94, 96, and the bifurcation 92 is injection molded over the entire proximal end of the core member 91 and a portion of the extension legs 32. Positioned distally of the bifurcation 92 and attached (e.g., bonded, mechanically connected, etc.) to the distal end of the core member 91 is a barbed clip connector 100, which has side slots 102 and an outer barb 104 configured to receive and engage a locking nut or collar 110. As with the embodiment shown in FIGS. 1-2, the two cannulae 94, 96 extend distally of the clip connector 100 and are sized for insertion into a dual lumen catheter shaft. FIG. 3B illustrates a connected system after the cannulae 94, 96 have been inserted into the lumens of the catheter shaft and the collar 110 is slid in a proximal direction from over the catheter shaft into locking relation with the clip connector 100. Once this locking connection has been established, the collar 110 freely rotates about the clip connector 100 and catheter shaft 20.

FIG. 3C illustrates a cross-sectional view of FIG. 3B, showing the engaged components. From this view, the barbed clip connector (collet) 100 can be seen as slightly shorter in length than that of the earlier described collet embodiment, with an internal ridge or ridges 106 to engage the catheter shaft 20. Also in this view, the interior of the collar 110 is shown, including a proximal barb 114 that is pressed over the external barb 104 of the connector 100 to provide a locking connection therebetween. The collar 110 also includes a compression ring 116 that in this embodiment is longer with respect to the overall length of the collar 110 than that of the embodiment in FIGS. 1-2. The attachment of collar 110 to connector 100 includes sliding the collar 110 over the catheter shaft 20 and onto the connector 100 until the barb 114 snaps or fits over the barb 104 such that an audible or tactile indication is provided. The side slots 102 facilitate the attachment process by permitting the connector 100 to flex.

Figure 4A:
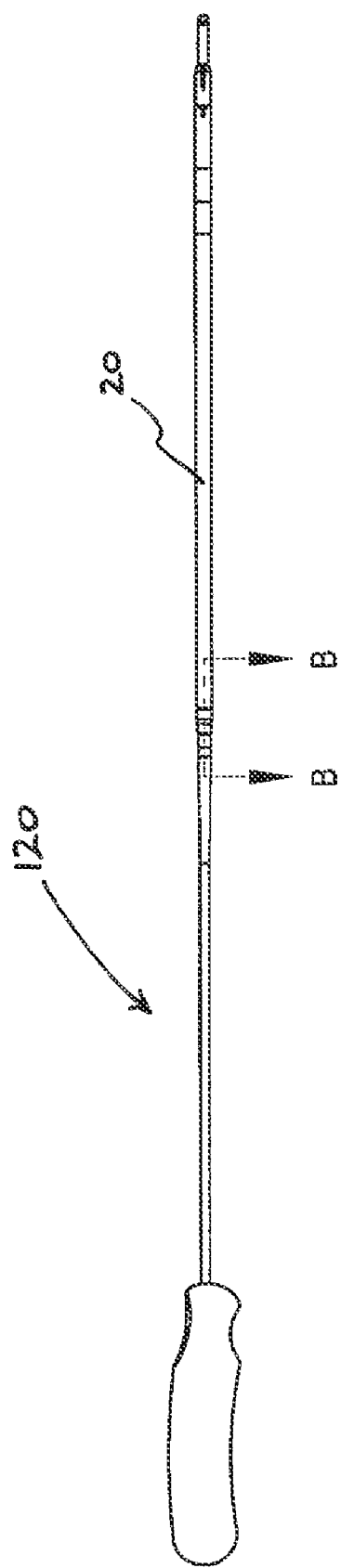
FIG. 4A is a side view of a tunneler attached to a multi-lumen catheter shaft via a multifunction adaptor.
Figure 4B:
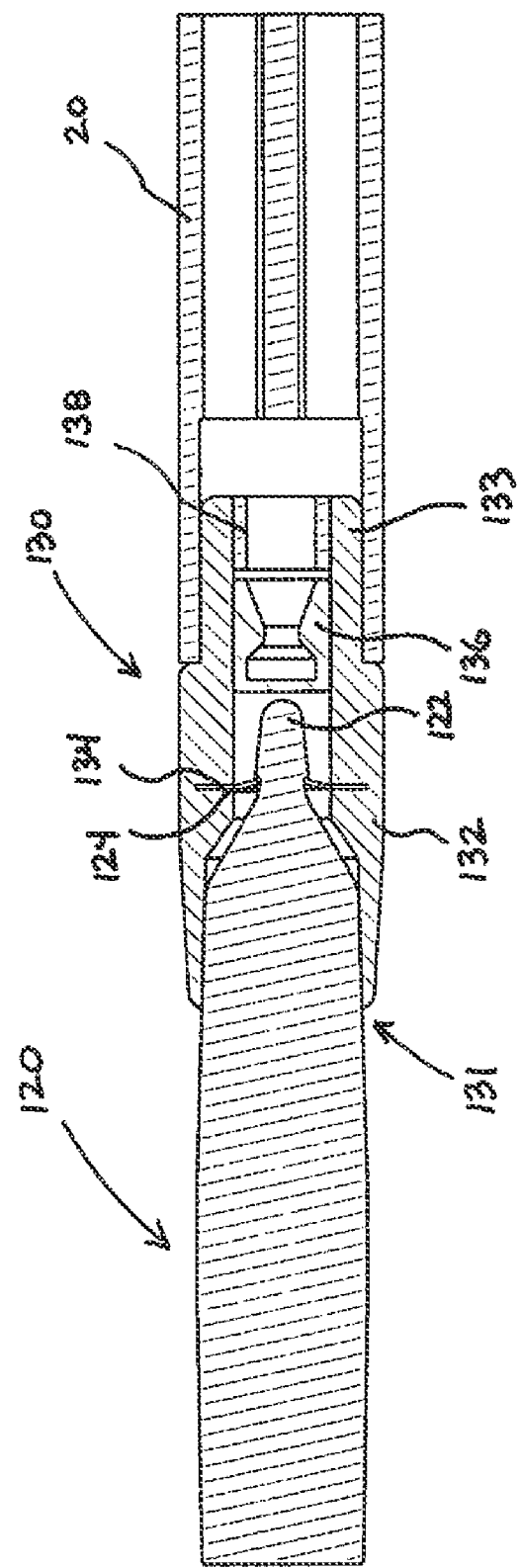
FIG. 4B is a cross-sectional view, taken along the line B-B, of the multi-lumen catheter shaft and tunneler of FIG. 4A, along with one embodiment of a multifunction adaptor.
Figure 4C:
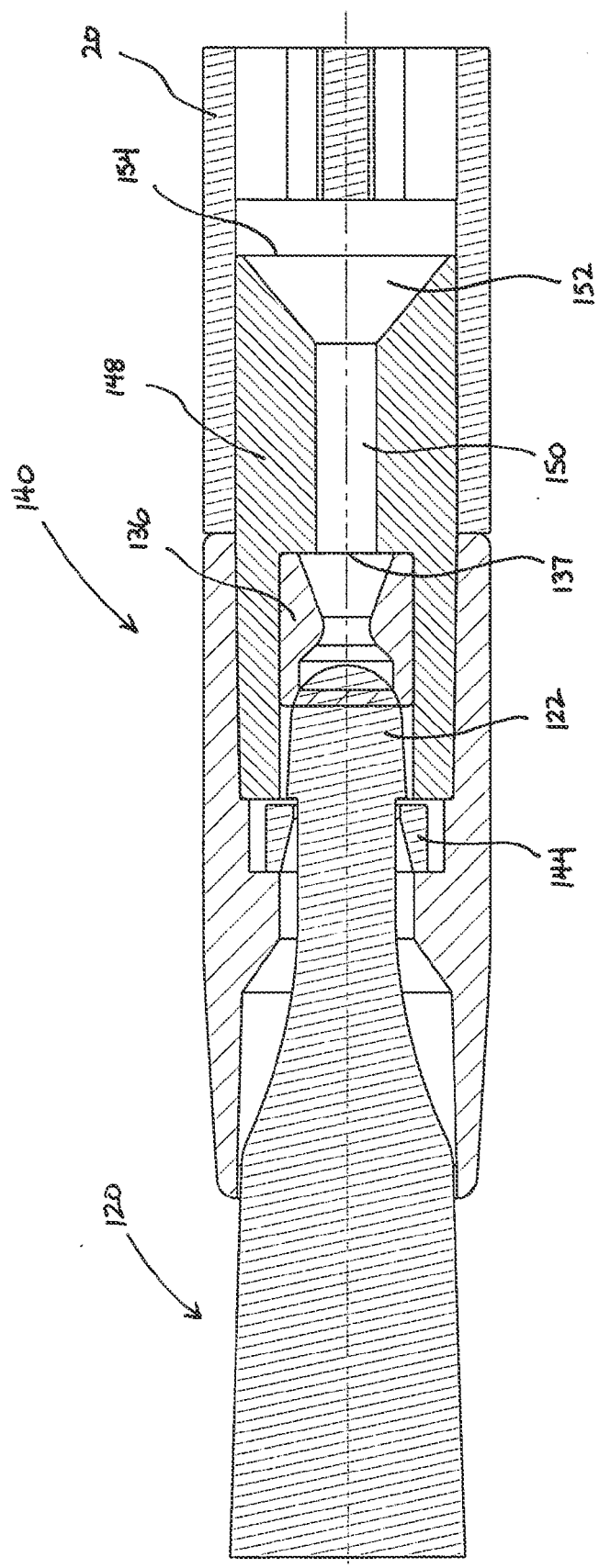
FIG. 4C is a cross-sectional view, taken along the line B-B, of the multi-lumen catheter shaft and tunneler of FIG. 4A, along with another embodiment of a multifunction adaptor.

FIG. 4A is a side view of a tunneler 120 connected to a catheter shaft, such as the catheter shaft 20 shown in FIG. 1, and FIGS. 4B and 4C are cross-sectional views of the connection between the catheter shaft 20 and tunneler 120 along section B-B, each showing a different embodiment for a multifunction adaptor, which is used to establish a connection between a catheter and another instrument. Examples of multifunction adaptors are illustrated and described in U.S. Application Publication No. 2005/0209584 ("Multifunction Adaptor for an Open-Ended Catheter"), published Sep. 22, 2005, and U.S. Application Publication No. 2005/0261664 ("Multifunction Adaptor for an Open-Ended Catheter"), published Nov. 24, 2005, each of which is expressly incorporated by reference as if fully set forth herein. In FIG. 4B, the distal end of the tunneler 120 is shown inserted into one embodiment of a multifunction adaptor 130, which in turn is inserted into a proximal end of a catheter shaft 20. In the view of FIG. 4B, the components of the multifunction adaptor 130 can be seen, including a housing 132, a retention disk 134, a guidewire valve 136 and a retention ring 138. The housing 132 has a proximal end that is tapered to streamline the connection between the tunneler 120 and the adapter 130 such that when the combination is pulled through subcutaneous tissue of a patient, a smooth profile is provided. The distal end of the housing has a section 133 with a smaller diameter than the proximal end of the housing, fashioned to be inserted into the proximal end of a catheter shaft 20 modified such that a proximal section is provided without an internal divider or septum, thereby permitting insertion of the distal end section 133 of the multifunction adaptor 130. When the distal end section 133 of the adaptor housing 132 is inserted into the proximal end of the catheter shaft 20, the outer surfaces of the catheter shaft 20 and housing 132 are approximately equal to provide a smooth transition.

The proximal end of the adaptor 130 has an opening 131 configured to receive a tunneler and/or tip of a syringe and an inner lumen that tapers to a smaller diameter where the retention disk is located. This taper is configured to engage a tunneler tip or syringe tip inserted therein to provide additional gripping of the inserted instrument such that inadvertent disengagement is avoided. The retention disk 134 is a component that has an opening to receive a tip 122 of the tunneler 120 therethrough (as shown), the sides of the opening flexing upon insertion and then catching on a shoulder 124 of the tunneler tip 122 to prevent disengagement. Within the distal portion of the adaptor lumen, a guidewire valve 136 is positioned to allow passage of a guidewire therethrough while preventing flow of fluid (e.g., blood) through the adaptor 130. When a syringe (not shown) is inserted into the proximal end 131 of the adaptor 130 and fluid is pushed therethrough, the valve 136 opens to permit passage of the fluid through the adaptor 130 and into the catheter shaft 20. Positioned distal of the valve 136 within the adaptor lumen is a retention ring 138 utilized to prevent the guidewire valve 136 from movement out of the adaptor. Of course, other means for preventing movement of the guidewire valve would be equally suitable, such as a ring of adhesive, etc. As illustrated, the multifunction adaptor 130 is attached to the proximal end of the catheter shaft 20 by solvent bonding and the guidewire valve 136 and retention ring 138 are likewise attached to the multifunction adaptor. However, this is only one possible method of attachment and other suitable methods are also possible (e.g., adhesive bonding, mechanical bonding, etc.) and are contemplated herein.

Figure 4D:
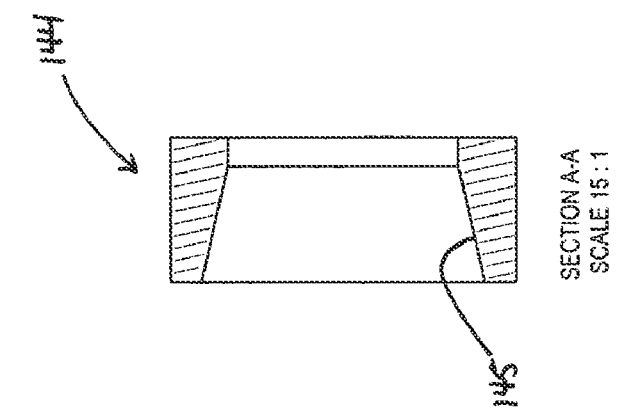
FIG. 4D is three views (perspective, side, and cross-sectional) of a C-clip.
Figure 4D:
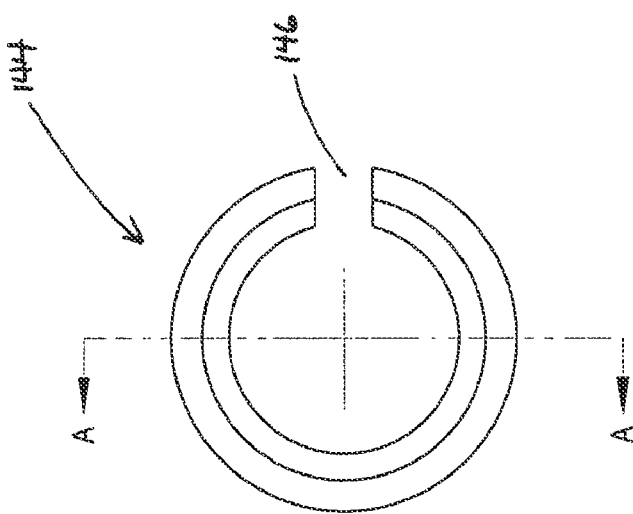
Figure 4D:
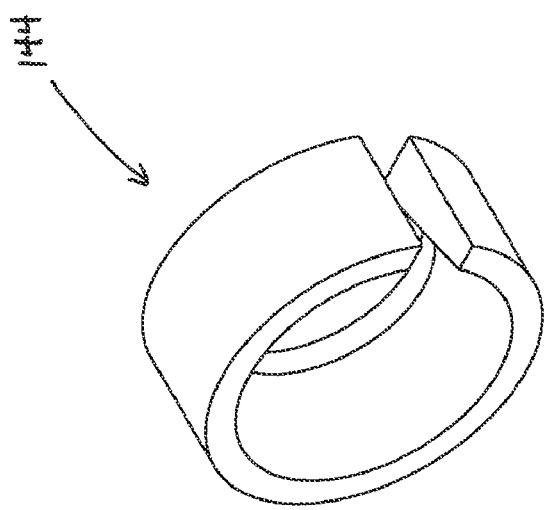

FIG. 4C illustrates another embodiment of a multifunction adaptor 140. In this embodiment, a C-clip 144 is positioned in the proximal end of the adaptor 140, instead of the retention disk 134 of adaptor 130, to capture and retain the tip 122 of a tunneler 120 inserted therethrough. FIG. 4D illustrates a perspective view, a side view, and a cross-sectional view of a C-clip 144. In the perspective view and side view, a break 146 between sides of the C-clip 144 can be seen, which permits the C-clip to flex (elastically deform) when an instrument is inserted therethrough. Following passage of the instrument, the C-clip recovers to its original shape. As shown in the cross-sectional view, the C-clip has a tapered lead-in 145 to guide the tunneler tip 122 into the center of the clip 144 and facilitate insertion of the tunneler tip 122 therethrough. The tunneler tip 122 is shown having a distal end within the valve 136, but depending on the length of the adaptor 140, in other embodiments the tip may not extend into the valve 136. In this particular embodiment, the adaptor 140 has a relatively short length to facilitate the tunneling procedure. The fact that the tip 122 extends into the valve is of little concern for this particular procedure, as the valve is no longer necessary to provide functionality after the tunneler 120 is inserted into the adaptor 140.

The multifunction adaptor in FIG. 4C, also includes a nose cone tube 148, which is positioned partially within the adaptor lumen in a distal portion thereof, extending outside of the adaptor housing 142 for insertion into a proximal end of a modified catheter shaft 20 (rather than the distal end of the adaptor housing as with the embodiment of FIG. 4B). In addition to providing a means for connecting the multifunction adaptor 140 to the catheter shaft 20, the nose cone tube 148 also acts to secure the guidewire valve 136 within the adaptor lumen. The nose cone tube 148 includes a first lumen section 150 in a proximal end and a second lumen section 152 in a distal end. The first lumen section 150 has a substantially constant diameter, which as shown is less than the diameter of the distal opening 137 of the valve 136 (although the diameter of the first lumen section 150 in other embodiments may be greater than or substantially equivalent to the diameter of the distal opening). The second lumen section 152 is shown with a diameter that progressively increases from the junction with the first lumen section to the distal opening 154, although constant diameters are also possible along all or a portion of the length of the second lumen section 152.

Figure 4E:
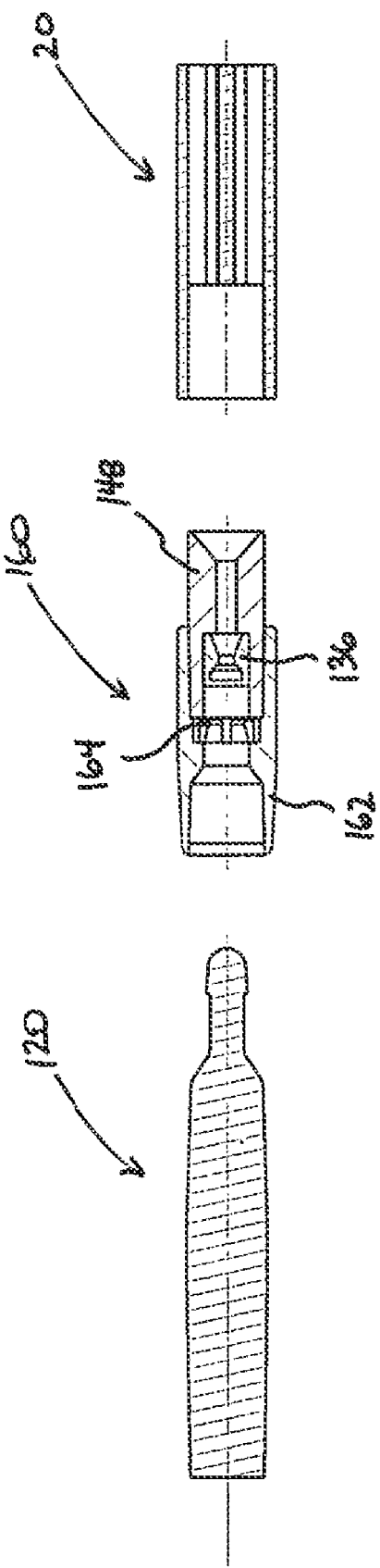
FIG. 4E is a cross-sectional perspective view of another embodiment of a tunneler, catheter shaft and multifunction adaptor.

FIG. 4E illustrates a cross-sectional exploded view of a tunneler 120, modified catheter shaft 20 and multifunction adaptor 160. Similar to adaptor 150, the adaptor 160 includes a housing 162, a valve 136 and a nose cone tube 148. However, rather than a C-clip, the adaptor 160 includes a formed surface 164 in a proximal end of the adaptor lumen, which functions similarly to the C-clip 144 (and the retention disk 134) to engage the tip 122 of the tunneler 120 and provide a locking connection therebetween.

Figure 5A:
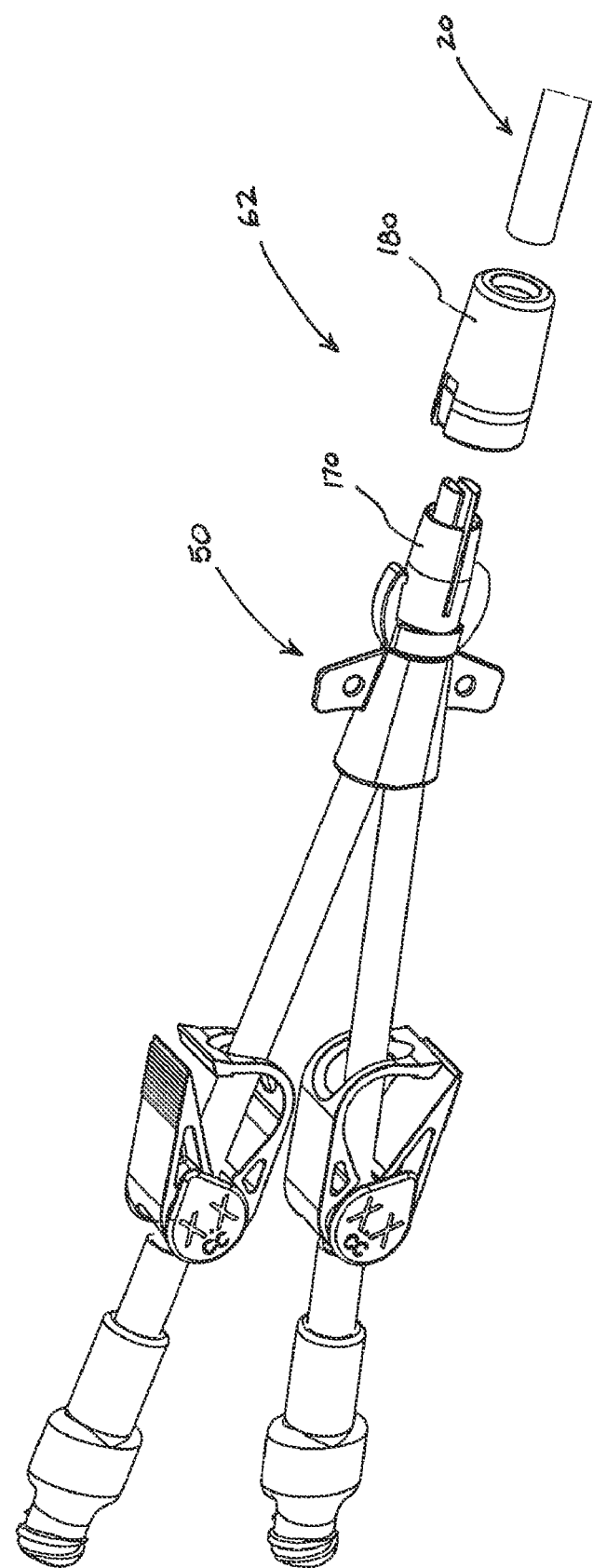
FIG. 5A is an exploded view of another embodiment of a connection system.
Figure 5B:
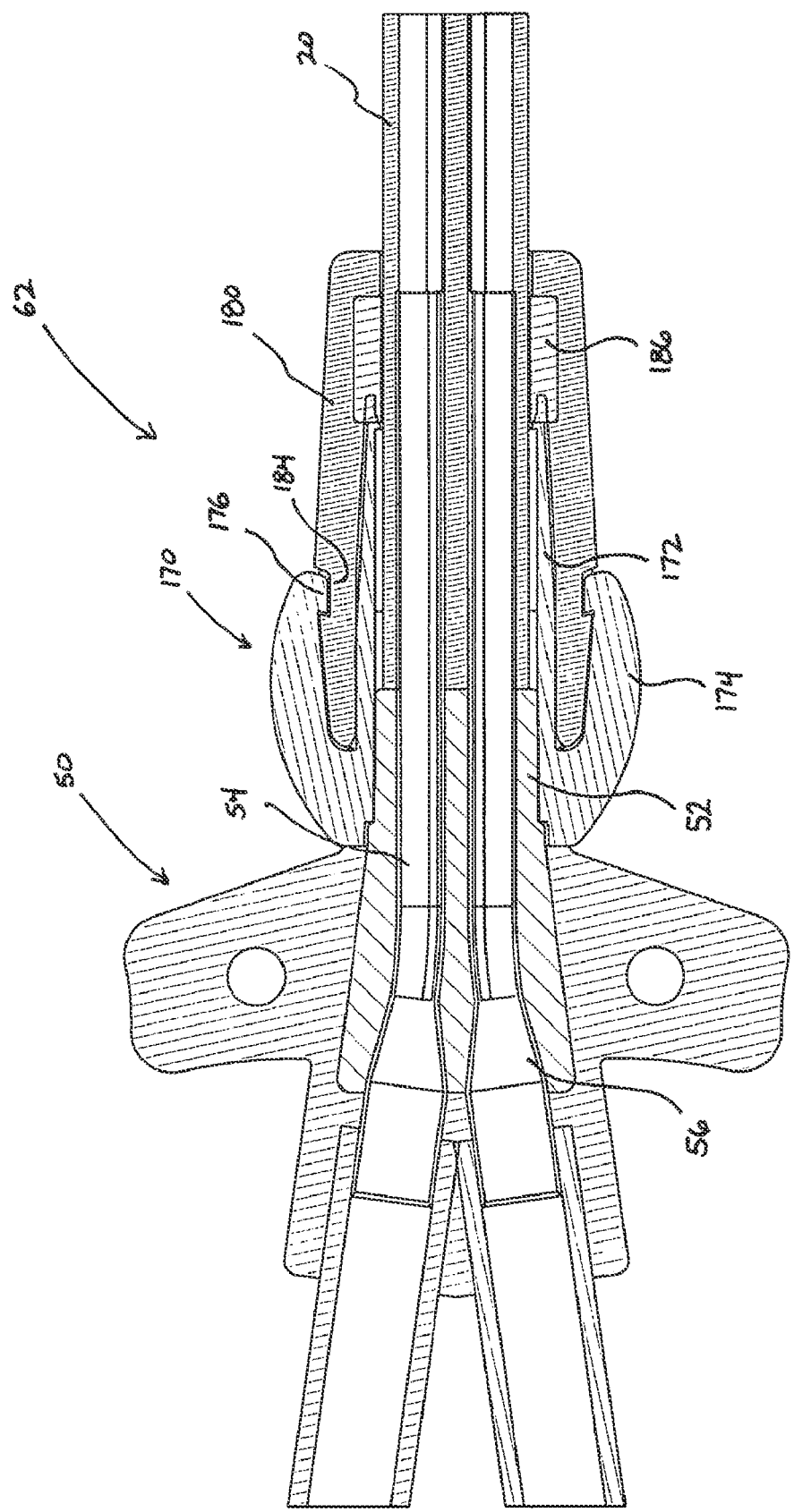
FIG. 5B is a longitudinal cross-sectional view of the connection system of FIG. 5A, showing a catheter connected to a hub assembly.

FIGS. 5A-5B illustrate another embodiment of a connection system for a multi-lumen catheter, including hub assembly 50 and connector assembly 62. FIG. 5A shows a perspective view of the connector assembly 62 with collet 170 and collar 180. FIG. 5B illustrates a cross-sectional view of the connector assembly 62 with the catheter shaft 20 connected to the hub assembly 50. Collet 170 includes a body 172 and locking arms 174 with protrusions 176 at a distal end configured to lockingly engage a recess 184 of the collar 180. The collet 170 has a proximal end attached to a distal end of the core member 52 such that the body 172 extends parallel to the cannulae 54, 56, but spaced apart therefrom to permit passage of a catheter wall between the collet body 172 and the cannulae 54, 56. In addition to the recess 184, the collar 180 includes a compression ring 186 positioned along a distal inner surface. To connect the catheter 20 to the bifurcation assembly 50, the catheter 20 is pushed through the collar 180 and over the distal ends of the cannulae 54, 56. The collar 180 is then pushed proximally over the catheter 20 and the collet 170 such that the recesses 184 are aligned with the locking arms 174. The collar 180 is finally pushed proximally until the protrusions 176 of the locking arms 174 fall into the recesses 184, which action provides an audible and/or tactile indication to the user to confirm connection. The arms 174 flex outward slightly as the collar is pushed proximally to provide a tight fit upon connection.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A catheter connection system, comprising:
   a hub assembly including a cannula extending from a distal end thereof, and a collet defining an inner surface spaced apart from the cannula to permit passage of a catheter wall between the collet inner surface and the cannula, the collet including a proximal barb on an outer surface thereof; and
   a collar including a compression ring positioned along a distal inner surface of the collar and contained within the collar, and an attachment barb positioned on a proximal inner surface of the collar, the collar secured to the collet following positioning of the catheter wall between the inner surface of the collet and the cannula through engagement of the collet barb and the collar barb, the collar freely rotatable over the collet following engagement.

2. The catheter connection system according to claim 1, wherein the hub assembly includes a core member surrounding a proximal end of the cannula.

3. The catheter connection system according to claim 1, wherein the cannula comprises a first cannula member and a second cannula member to be received, respectively, in a first lumen and a second lumen of a multi-lumen catheter.

4. The catheter connection system according to claim 3, further comprising a bifurcation molded over a proximal end of a core member, the bifurcation including a first extension tube in fluid communication with the first cannula and a second extension tube in fluid communication with the second cannula.

5. The catheter connection system according to claim 3, wherein the first and second cannula members are slightly larger than the first and second lumens such that a compressive fit is formed when the cannula members are slid into the lumens.

6. The catheter connection system according to claim 1, wherein the collet outer surface further comprises one or more threads.

7. The catheter connection system according to claim 6, wherein the collar inner surface further comprises one or more threads that interact with the collet threads.

8. The catheter connection system according to claim 7, wherein the collet threads are spaced apart from the collar threads following engagement of the collet barb and the collar barb.

9. The catheter connection system according to claim 1, wherein the collet outer surface includes a tapered distal section.

10. The catheter connection system according to claim 1, wherein the collet inner surface includes a plurality of ridges.

11. A method of connecting a catheter connection system to a catheter, comprising:
   providing a hub assembly including a cannula extending from a distal end thereof, and a collet defining an inner surface spaced apart from the cannula and a proximal barb on an outer surface thereof;
   sliding a catheter over the cannula such that a wall of the catheter passes between the cannula and collet inner surface;
   moving a collar over the catheter and onto the collet, the collar including a compression ring positioned along a distal inner surface of the collar and contained within the collar, and an attachment barb positioned on a proximal inner surface of the collar; and
   engaging the collet barb and the collar barb through proximal movement of the collar barb over the collet barb, the collar permanently connected to the collet and the collar freely rotatable about the collet following the engaging.

12. The method according to claim 11, wherein the cannula comprises a first cannula member and a second cannula member, the sliding step further comprising sliding a first catheter lumen and a second catheter lumen of a multi-lumen catheter simultaneously over the first and second cannula members.

13. The method according to claim 12, wherein the first and second cannula members are slightly larger than the first and second catheter lumens, the sliding step further comprising providing a compressive fit between the first and second cannula members and the first and second catheter lumens.

14. The method according to claim 11, wherein the collet outer surface includes one or more threads and the collar inner surface includes one or more threads that interact with the collet threads, the moving step further comprising twisting the collar onto the collet prior to the engaging step.

15. The method according to claim 14, wherein following the engaging step, the collet threads are spaced apart from the collar threads.

16. The method according to claim 14, wherein the collet comprises an inner surface including one or more ridges, the moving step including radially compressing the collet such that the ridges engage an outer surface of the catheter.

17. The method according to claim 11, wherein the engaging step further comprises providing an audible or tactile indication to verify engagement between the collar and collet.

18. A method of connecting a catheter connection system to a catheter, comprising:
  providing a hub assembly including:
    first and second cannula members extending in parallel relation from a distal end of the hub assembly;
    first and second extension tubes in fluid communication, respectively with the first and second cannula members;
    a core member surrounding a proximal portion of the first and second cannula members and a distal portion of the first and second extension tubes; and
    a collet having an inner surface spaced apart from the cannula and a threaded outer surface including a proximal barb;
  sliding a multi-lumen catheter including a first and second lumen over the first and second cannula members such that a wall of the catheter passes between the cannula members and the collet inner surface;
  moving a collar over the catheter and onto the collet, the collar including a compression ring secured to a distal inner surface of the collar and a threaded inner surface with an attachment barb;
  twisting the collar onto the collet through interaction of the respective threaded surfaces; and
  engaging the collar attachment barb and the collet proximal barb through proximal movement of the collar attachment barb over the collet proximal barb, the collar permanently connected to the collet and freely rotatable over the collet following the engaging.

19. The method according to claim 18, wherein the collet comprises an inner surface including one or more ridges, the twisting step including radially compressing the collet such that the ridges engage an outer surface of the catheter.

* * * * *